(12) United States Patent
Bofarull et al.

(10) Patent No.: US 7,728,000 B2
(45) Date of Patent: Jun. 1, 2010

(54) SUBSTITUTED QUINOLINES FOR THE TREATMENT OF CANCER

(75) Inventors: Juan Aymami Bofarull, Barcelona (ES); Miquel Coll Capella, Madrid (ES); Amadeo Llebaria Soldevila, Madrid (ES); Isabel Navarro Muñoz, Barcelona (ES)

(73) Assignees: Crystax Pharmaceuticals, Barcelona (ES); Universitat Politecnica de Catalunya, Barcelona (ES); Consejo Superior de Investigactiones Cientificas, Madrid (ES)

(*) Notice: Subject to any disclaimer, the term of this patent is extended or adjusted under 35 U.S.C. 154(b) by 991 days.

(21) Appl. No.: 10/580,140

(22) PCT Filed: Nov. 18, 2004

(86) PCT No.: PCT/EP2004/013106

§ 371 (c)(1),
(2), (4) Date: May 19, 2006

(87) PCT Pub. No.: WO2005/054236

PCT Pub. Date: Jun. 16, 2005

(65) Prior Publication Data

US 2007/0105784 A1 May 10, 2007

(30) Foreign Application Priority Data

Nov. 20, 2003 (ES) .................................. 200302821

(51) Int. Cl.
*A61K 31/4745* (2006.01)
*C07D 471/04* (2006.01)
(52) U.S. Cl. ........................................ 514/285; 546/62
(58) Field of Classification Search ................. 514/285; 546/62
See application file for complete search history.

(56) References Cited

FOREIGN PATENT DOCUMENTS

WO           98/45272 A      10/1998

OTHER PUBLICATIONS

Tugusheva, N.Z. et al, Synthesis of 2,10,11-Trisubstituted Indolo [3,2-b] Quinolines, Chemistry of Heterocyclic Compounds, 1511-1517, 38 (12), 2002, Plenum Publishing Corporation, New York, NY.
Eritja, Ramon, Synthesis and Properties of Oligonucleotides Carrying Cryptolepine Derivatives, Chemistry and Biodiversity, 289-295, 1 (2), 2004, Verlag Helvetica Chimica Acta AG, Barcelona, Spain.
Yang, Shu-Wei et al, Synthesis and Biological Evaluation of Analogues of Cryptolepine, an Alkaloid Isolated from Suriname Rainsforest, Journal of Natural Products, Jun. 3, 1999, 976-983, 62 (7), American Chemical and American Society of Pharmacognosy.
Sharaf, Maged H.M. et al, Cryptolepinone vs. Hydroxycryptolepine: a Resolution of a Question of Substituent Functionality and Double Bond Isomerization, Journal of Heterocyclic Chemistry, 1365-1369, 35 (6) (1998).
Chen, Junjie et al, Synthesis and Cytotoxic Activity of N-(2-Diethylamino) ethylcarboxamide and Other Derivatives of 10H-Quindoline, Bioorganic & Medicinal Chemistry, 2381-2386, 10 (7) (2002).
Wright, Colin W. et al, Synthesis and Evaluation of Cryptolepine Analogues for their Potential as New Antimalarial Agents, Journal of Medicinal Chemistry, Aug. 18, 2001, 3187-3194, 44 (19), American Chemical Society.
Takeuchi Y et al, Synthesis and Antitumor Activity of Fused Quinoline Derivatives.IV.Novel 11-aminoindolo [3,2-b] quinolines, Chemical and Pharmaceutical Bulletin, Pharmaceutical Society of Japan, 406-411, vol. 45 No. 2, Feb. 1997.
Goerlitzer K et al, Ueber 10-H-Indolo[3,2-b]chinolin-5-oxid (Oxychindolin) und seine Derivate, Pharmazie, Veb Verlag Volk Und Gesundheit, 919-926, vol. 52 No. 12, 1997, Berlin, Germany.
Database Beilstein Beilstein Institute for Organic Chemistry, Frankfurt-Main, Germany XP002325168, and Chem. Pharm. Bull, vol. 40 No. 2, 1992, pp. 528-530.
Database Beilstein Beilstein Institute for Organic Chemistry, Frankfurt-Main, Germany XP002325169, and J. Chem. Soc, 1948, p. 922.

*Primary Examiner*—Charanjit S Aulakh
(74) *Attorney, Agent, or Firm*—Peter B. Scull; Kristina M. Kalan; Berenbaum Weinshienk PC

(57) ABSTRACT

Compounds of formula $G_1$-L-$G_2$, where -$G_1$ is a radical structurally close to cryptolepine, -L- is a single covalent bond or a covalent linking biradical selected from $(CH_2)_rNR'''(CH_2)_s$ and —$(CH_2)_rNR'''(CH_2)_sNR''''(CH_2)_t$—, —R''' and —R'''' are radicals, same or different, selected from the group consisting of H and $(C_1$-$C_3)$-alkyl; r, s and t are an integer from 1 to 3 and, -$G_2$ is H or a radical structurally close to -$G_1$, are intercalators. They are compounds which intercalate between DNA base pairs, and are useful as therapeutic agents against cancer, as assess by an in vitro test of cytotoxicity with human leukemia cells Jurkat E6-1 and human carcinoma cells GLC-4. Preferred compounds are those where -$G_1$ is bonded to -L- through a carbonyl amino and -L- is —$(CH_2)_3NCH_3(CH_2)_3$ or —$(CH_2)_2NCH_3(CH_2)_sNCH_3(CH_2)_2$— where s =2 or 3. -$G_1$ is a radical selected from (IIa) y (IIb); -$G_2$ is a radical selected from H, a radical of formula (IIa), a radical of formula (IIb), the N-radical of 1,8-naphthalimide, the C4-radical of 2-phenylquinoline, and the C9-radical of acridine.

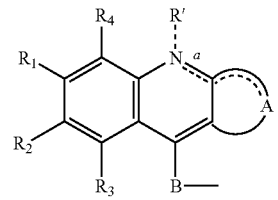

(IIa)

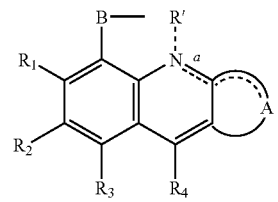

(IIb)

16 Claims, No Drawings

SUBSTITUTED QUINOLINES FOR THE TREATMENT OF CANCER

CROSS-REFERENCE TO RELATED APPLICATIONS

The present application is the US national stage application of the Patent Cooperation Treaty (PCT) Application Number PCT/EP2004/013106 filed 18 Nov. 2004, entitled "SUBSTITUTED QUINOLINES FOR THE TREATMENT OF CANCER"; which designated all states including the United States of America; the subject matter of which hereby being specifically incorporated herein by reference for all that it discloses and teaches; and claims priority from the Spanish Patent Application, Number P200302821, filed 20 Nov. 2003, the subject matter of which also hereby being specifically incorporated herein by reference for all that it discloses and teaches.

This invention relates to new compounds which intercalate between DNA base pairs. Such compounds can be used for the treatment of cancer.

BACKGROUND ART

Intercalators are a group of compounds that bind between the DNA base pairs. This intercalation can produce an interruption of transcription, replication and/or topoisomerase activity. It has been found that many compounds that bind to DNA by intercalation have antiproliferative properties and in vivo antitumour effects. Intercalators have been used as anticancer drugs. Cryptolepine is a naturally occurring alkaloid and it is used in traditional medicine against malaria. Its formula, shown below, is structurally close to some compounds of the present invention. Cryptolepine is able to bind CG-rich sequences of DNA containing non-alternating CC sites, and it has been reported as potential anticancer drug (cf. e.g. J. N. Lisgarten et al., "The antimalarial and cytotoxic drug cryptolepine intercalates into DNA at cytosine-cytosine sites", Nature Structural Biology 2002, vol. 9, pp. 57-60). Thus, the provision of new intercalators with anticancer activity is highly desirable.

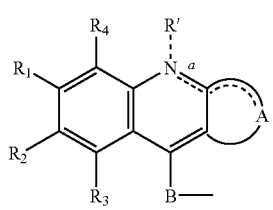

SUMMARY OF THE INVENTION

According to an aspect of the present invention, there is provided a compound of formula (I), $$G_1\text{-}L\text{-}G_2 \qquad (I)$$

or a pharmaceutically acceptable salt thereof, wherein:
-$G_1$ is a radical selected from (IIa) y (IIb);

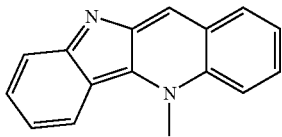
(IIa)

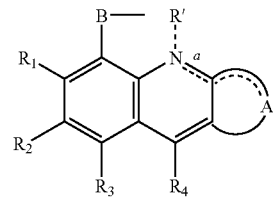
(IIb)

wherein —R' is an electron pair or a ($C_1$-$C_3$)-alkyl radical; with the condition that (i) when —R' is an electron pair, a is a N═C double bond and the fused ring

is the biradical

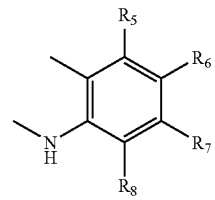

thus radicals (IIa) and (IIb) are respectively (IIa') and (IIb'), and

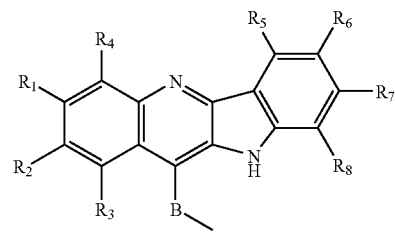
(IIa')

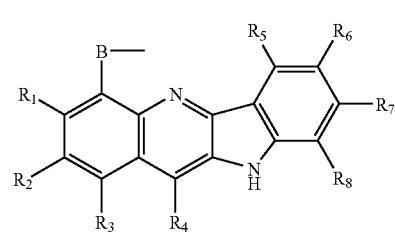
(IIb')

(ii) when —R' is a ($C_1$-$C_3$)-alkyl radical, a is a N—C single bond and the fused ring is the triradical

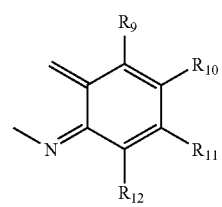

thus radicals (IIa) and (IIb) are respectively (IIa") and (IIb");

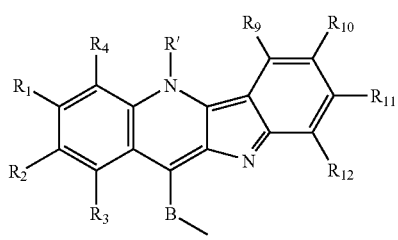

(IIa")

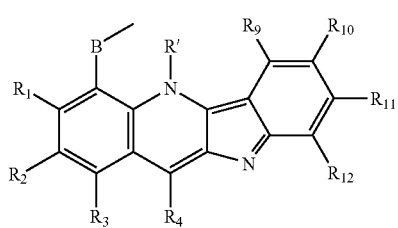

(IIb")

wherein —$R_1$ to —$R_{12}$ represent radicals, same or different, selected from the group consisting of H, ($C_1$-$C_4$)-alkyl, ($C_1$-$C_4$)-alkoxy, ($C_1$-$C_4$)-alkylamino, phenyl, F, Cl, Br, amino, hydroxy, and nitro;

and wherein —B— is a biradical selected from the group consisting of —CONH—, —$NR_{13}$—, —O—, —$(CH_2)_n$NH—, —$(CH_2)_n$O—, —CONH$(CH_2)_u$Z—, —CONH$(CH_2)_u$CH$(CH_2$OH$)CH_2$Z— and —CO[NHCHR"CO]$_m$O—; wherein —$R_{13}$ is selected from the group consisting of H, ($C_1$-$C_4$)-alkyl, ($C_1$-$C_4$)-alkoxy and ($C_1$-$C_4$)-alkylamino; —R" are side chains radicals, same or different, corresponding to natural aminoacids; n is an integer from 1 to 3; m is an integer from 1 to 3; u is an integer from 1 to 3, and —Z— is a biradical of a oligonucleotide phosphate between 4 and 23 bases in length, linked to the methylene group at the 5' end or at the 3' end;

-L- is a single covalent bond or a covalent linking biradical selected from the following ones;

wherein —R'" and —R"" are radicals, same or different, selected from the group consisting of H and ($C_1$-$C_3$)-alkyl; r is an integer from 1 to 3; s is an integer from 1 to 3; t is an integer from 1 to 3; and -$G_2$ is a radical selected from H, a radical of formula (IIa), a radical of formula (IIb), the N-radical of 1,8-naphthalimide, the C4-radical of 2-phenylquinoline, and the C9-radical of acridine;

with the proviso that (I) is not one of the compounds of the following list, which have been previously described (the Chemical Abstracts Registry number, CAS RN, is given) but not for the industrial applicability of the present invention. The corresponding values for radicals in formula (I) are also included:

10H-quindoline-11-carboxamide (CAS RN 367911-30-6; -$G_1$=IIa'; —B—=—CONH—; —R'=electron pair; —$R_1$ to $R_8$=H; -L-=single covalent bond; -$G_2$=—H);

2-bromo-10H-quindoline-11-carboxamide (CAS RN 241470-56-4; -$G_1$=IIa'; —B—=—CONH—; —R'=electron pair; —$R_2$=—Br; —$R_1$, —$R_3$ to —$R_4$, —$R_5$ to —$R_8$=H; -L-=single covalent bond; -$G_2$=—H);

N-10H-quindolin-11-yl-1,3-propanediamine (CAS RN 188630-48-0; -$G_1$=IIa'; —B—=—NH—, —R'=electron pair; —$R_1$ to —$R_4$, —$R_5$ to —$R_8$=—H; -L-=—$(CH_2)_3$NH—; -$G_2$=—H);

10H-quindolin-11-amine monohydrochloride (CAS RN 164406-49-9; -$G_1$=IIa', —B—=—NH; —R'=electron pair; —$R_1$ to —$R_4$, —$R_5$ to —$R_8$=—H; -L-=single covalent bond; -$G_2$=—H);

10H-quindolin-11-methanol (CAS RN 241470-44-0; $G_1$=IIa'; —B—=—$CH_2$O—; —R'=electron pair; —$R_1$ to —$R_4$, —$R_5$ to —$R_8$=H, -L-=single covalent bond, -$G_2$=—H); or N-[2-(dimethylamino)ethyl]-10-H-quindoline-4-carboxamide (CAS RN 191172-25-5; $G_1$=IIb'; —B—=—CONH—; —R'=electron pair; —$R_1$ to —$R_4$, —$R_5$ to —$R_8$=—H, -L-=—$(CH_3)_2$N$(CH_3)CH_2$—, -$G_2$=—H).

In a preferred embodiment, compounds of formula (I) are those where (IIa) is the radical (IIa').

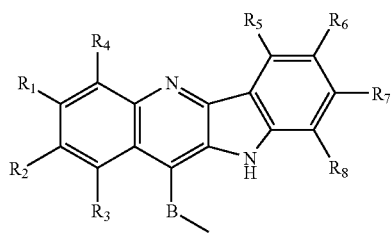

(IIa')

Preferred compounds are those of formula (I) where (IIa) is (IIa') and —B— is —CONH— or —$NR_{13}$—. Also preferred are those of formula (I) where (IIa) is (IIa') and —B— is —CO[NHCHR"CO]$_m$O— and more preferred are the compounds where m=2, the leftward —R" is a glicine side chain, and the rightward —R" is a arginine side chain. Also preferred compounds are those of formula (I) where (IIa) is (IIa') and —B— is —CONH$(CH_2)_u$Z— or —CONH$(CH_2)_u$CH$(CH_2$OH$)CH_2$Z—. More preferred are the compounds where —Z— is -TTCCGGAA-linked at 3' end or at 5' end, or -CT-TCTTCTTCT-linked at 3' end. Specially preferred are those where -L- is a single covalent bond. Also specially preferred are those where -L- is a covalent linking biradical selected from the following ones.

The most preferred are the compounds where -L- is the biradical —$(CH_2)_r$NR'"$(CH_2)_s$—, —R'" is methyl and both r and s are 3, and the compounds where -L- is the biradical —$(CH_2)_r$NR'"$(CH_2)_s$NR""$(CH)_t$—, —R'" and —R"" are methyl; both r and t are 2 and s is an integer from 2 to 3.

In another preferred embodiment, compounds of formula (I) are those where (IIa) is the following radical.

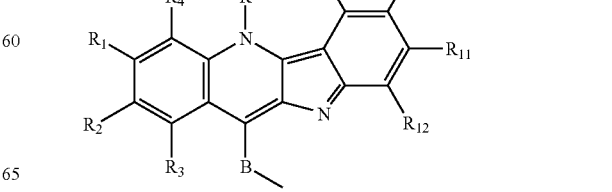

(IIa")

Preferred compounds are those where (IIa) is (IIa") and —B— is —CONH— or —NR$_{13}$—. Also preferred are those where —B— is —CO[NHCHR"CO]$_m$O—, and more preferred are the compounds where m=2, the leftward —R" is a glicine side chain, and the rightward —R" is a arginine side chain. Also preferred compounds are those of formula (I) where (IIa) is (IIa") and —B— is —CONH(CH$_2$)$_u$Z— or —CONH(CH$_2$)$_u$CH(CH$_2$OH)CH$_2$Z—. More preferred are the compounds where —Z— is -TTCCGGAA-linked at 3' or 5' end or —CTTCTTCTTCT-linked at 3' end. Even more preferred are those where —R' is methyl. Specially preferred are those where -L- is a single covalent bond. Also specially preferred are those where -L- is a covalent linking biradical selected from the following ones.

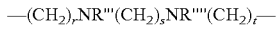

The most preferred are the compounds where -L- is the biradical —(CH$_2$)$_r$NR'''(CH$_2$)$_s$—, —R''' is methyl and both r and s are 3, and the compounds where -L- is the biradical —(CH$_2$)$_r$NR'''(CH$_2$)$_s$NR''''(CH$_2$)$_t$—, —R''' and —R'''' are methyl; both r and t are 2, and s is an integer from 2 to 3.

The most preferred compounds of formula (I) are those of the following list, whose preparation is described in the accompanying examples for the first time: N-[3-[[3-[(9-acridinecarbonyl)amino]propyl]methylamino]propyl]-10H-indolo[3,2-b]quinoline-11-carboxamide (Ia); N,N'-(4-methyl-4-azaheptamethylene)-di-(10H-indolo[3,2-b]quinoline-11,11'-carboxamide) (Ib); N-[3-[3-[[2-(1,3-dioxo-(2,3-dihydro)-1H-benzo[de]isoquinolinyl)propyl]methylamino]propyl]-10H-indolo[3,2-b]quinoline-11-carboxamide (Ic); N-[3-[[3-[2-phenyl-4-quinolinecarbonyl)amino]propyl]methylamino]propyl]-10H-indolo[3,2-b]quinoline-11-carboxamide (Id); N,N'-(3,7-dimethyl-3,7-diazanonamethylene)-di-(10H-indolo[3,2-b]quinoline-11,11'-carboxamide) (Ie); N-[(9-acridinecarbonyl)-3,7,10-triaza-3,7-dimethyldecyl]-10H-indolo[3,2-b]quinoline-11-carboxamide (If); N,N'-(3,6-dimethyl-3,6-diazaoctamethylene)-di-(10H-indolo[3,2-b]quinoline-11-11'-carboxamide) (Ig); N-[(9-acridinecarbonyl)-3,6-dimethyl-3,6-diazaoctamethylene]-10H-indolo[3,2-b]quinoline-11-carboxamide (Ih); N-[[1,3-dioxo-(2,3-dihydro)-1H-benzo[de]isoquinolyl]-3,6-dimethyl-3,6-diazaoctamethylene]-10H-indolo[3,2-b]quinoline-11-carboxamide (Ii); N-[[1,3-dioxo-(2,3-dihydro)-1H-benzo[de]isoquinolyl]-3,7,10-triaza-3,7-dimethyldecyl]-10H-indolo[3,2-b]quinoline-11-carboxamide (Ij); N,N'-(4-methyl-4-azaheptamethylene)-di-(methyl-5H-indolo[3,2-b]quinoline-11,11'-carboxamide) (Im); 10H-indolo[3,2-b]quinoline-11-carbonyl-glicine-arginine (Io); N,N-dimethyl-N'-(5-methyl-5H-indolo[3,2-b]quinolin-11-yl)-ethane-1,2-diamine (Ip); N,N'-(4-methyl-4-azaheptamethylen)-di-(10H-indolo[3,2-b]quinoline-11,11'-amine (Iq); N-1-[(5-hydroxymethyl-6-(5'-TTCCGGAA-3'-phosphate)-hexyl]-10H-indolo[3,2-b]quinoline-11 carboxamide (Ir); N-1-[(5-hydroxymethyl-6-(5'-CTTCCTCCTCT-3'-phosphate)-hexyl]-10H-indolo[3,2-b]quinoline-11-carboxamide (Is); and N-1-[6-(5'-phosphate-TTCCGGAA)-hexyl]-10H-indolo[3,2-b]quinoline-11-carboxamide (It); 10H-Indolo[3,2-b]quinoline-11-carboxylic acid (2-dimethylamino-ethyl)amide (Iu); 10H-Indolo[3,2-b]quinoline-11-carboxylic acid (2-dimethylamino-propyl)amide (Iv); N,N-dimethyl-N'-(5-methyl-5H-indolo[3,2-b]quinolin-11-yl)-propane-1,2-diamine (Iw); N-[3-[[3-[(10H-indolo[3,2-b]quinoline-4-carboxamide]propyl]methylamino]propyl]-10H-indolo[3,2-b]quinoline-11-carboxamide (Ix); N,N'-(3,7-dimethyl-3,7-diazanonamethylene)-di-(methyl-5H-indolo[3,2-b]quinoline-11,11'-carboxamide) (Iy); N,N'-(3,6-dimethyl-3,6-diazaoctamethylene)-di-(methyl-5H-indolo[3,2-b]quinoline-11,11'-carboxamide) (Iz); (3,7-diazanonamethylene)-di-(10H-indolo[3,2-b]quinoline-11,11'-carboxamide (Iaa); N,N'-(3,7-dimethyl-3,7-diazanonamethylene)-di-(10H-indolo[3,2-b]quinoline-11,11'-amine (Iab); N,N'-(3,6-dimethyl-3,6-diazaoctamethylene)-di-(10H-indolo[3,2-b]quinoline-11,11'-amine (Iac).

Another aspect of the present invention refers to the use of the compound of formula (I), defined above, for the preparation of a medicament for the treatment of cancer. A further aspect of the present invention relates to a pharmaceutical composition comprising as active ingredient a therapeutically effective amount of the compound of formula (I), defined above, together with suitable pharmaceutical excipients or carriers.

Compounds of formula (I) where biradical —B— in -G$_1$ is —CONH— and -G$_2$ is not the N-radical of 1,8-naphtalimide can be prepared according to the process summarized in Scheme I, where GP represents an amino protecting group. The process involves a coupling reaction of a compound of formula (Vb) with a compound of formula (III). The compound of formula (Vb) is prepared by reaction of a compound of formula (III) with a monoprotected bis-amine of formula (IV), followed by the removal of the amino protective group. Monoprotected bis-amines of formula (IV) are commercially available compounds or they can be prepared by methods known in the art (cf. Spicer et al., *Bioorg. Med. Chem.* 2002, vol. 10, p. 19; Deady et al., *Bioorg. Med. Chem.* 2000, vol. 8, p. 977). An example of amino protective group is the t-butoxycarbonyl (BOC).

Scheme I:

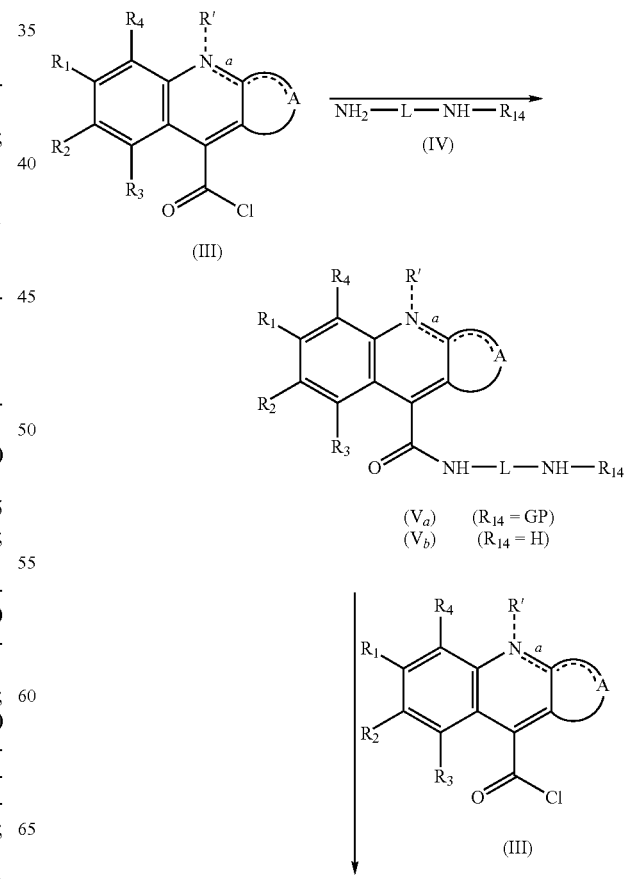

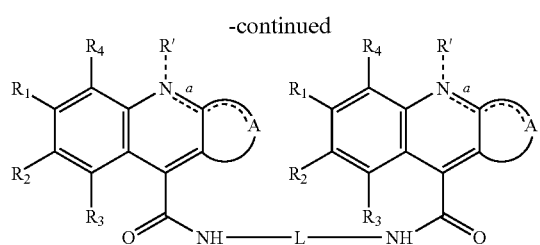

When biradical —B— in -G$_1$ is —CONH— and -G$_2$ is 1,8-naphthalamide, compounds of formula (I) can be obtained by the process summarized in Scheme II. This process involves the coupling reaction of a compound of formula (VII$_b$) with a compound of formula (III). The compound of formula (VII$_b$) can be prepared by reaction of 1,8-naphthalic anhydride (VI) with a monoprotected bis-amine of formula (IV), followed by the removal of the amino protective group.

Scheme II:

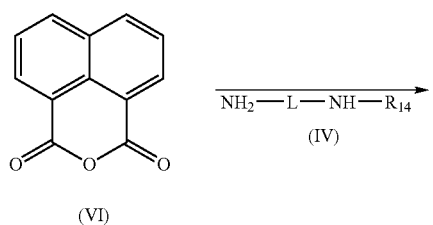

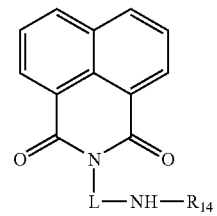

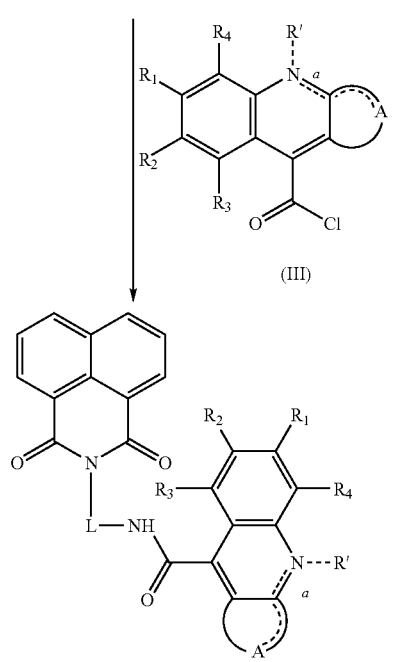

Compounds of formula (I) where —B— is a biradical selected from other groups as —NR$_{13}$—, —O—, —(CH$_2$)$_n$NH—, —(CH$_2$)$_n$O—, can be obtained analogously by using standards processes of organic chemistry, well known in the art for the production of such type of compounds. For example, for —B—=—NH— the process of Scheme III can be followed, as it has been done for the compound of the Example 15.

Scheme III:

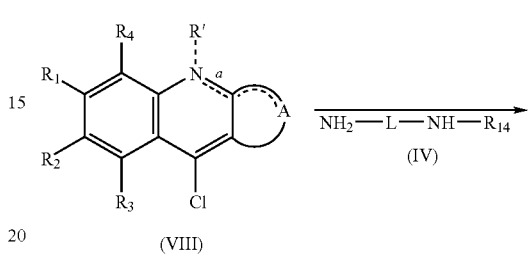

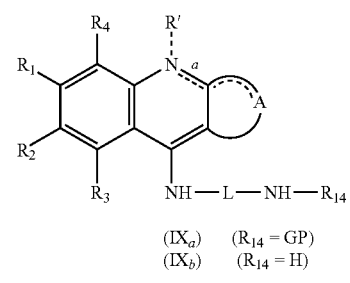

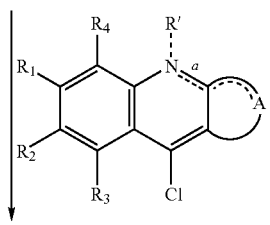

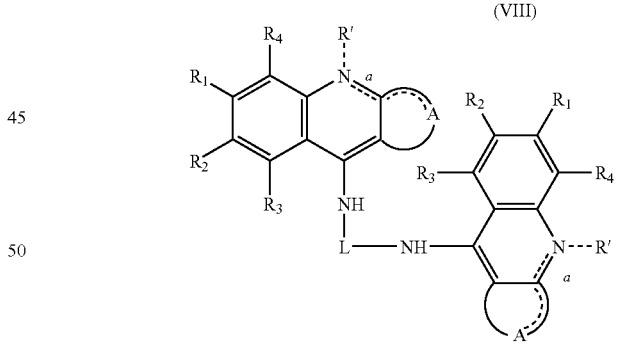

Compounds of formula (I) where biradical —B— is —CO[NHCHR"CO]$_m$O—, —R" is side chain radicals, same or different, corresponding to a natural aminoacid and m is an integer selected from 1 to 3, can be obtained by solid phase methods. The synthesis is carried out assembling a N-protected aminoacid or peptide in a p-methylbenzhydrilamine resine. After removal of the protective group, the 11-aminocarboxylic radical selected from formula (IIa) or the 4-aminocarboxylic radical selected from formula (IIb) is coupled by benzotriazol-1-yloxytripyrrolidinophosphonium hexafluoro-phosphate (PyBOP) and diusopropylamine, followed by acidolysis.

Compounds of formula (I) where —B— is a birradical selected from —CONH(CH$_2$)$_u$Z— or —CONH(CH$_2$)$_u$CH(CH$_2$OH)CH$_2$Z—, where u is an integer from 1 to 6, and -Z— is a biradical of a oligonucleotide phosphate between 4 and 23 bases in length, linked to the methylene group at 5' end or at 3' end can be prepared by conventional methods of peptide coupling in solid phase or solution phase. Compounds of formula (I) may be converted into pharmaceutically acceptable acid addition salts, and salts may be converted into free compounds, by conventional methods. For instance, the acid addition salts may be prepared by contacting the free base with an appropriate amount of the desired acid in a conventional manner.

Compounds of formula (I) are intercalators (i.e. compounds which intercalate between DNA base pairs) and, as illustrated by biological results in example 30 are active for cancer treatment.

Throughout the description and claims the word "comprise" and variations of the word, are not intended to exclude other technical features, additives, components, or steps. The abstract of this application is incorporated herein as reference. Additional objects, advantages and features of the invention will become apparent to those skilled in the art upon examination of the description or may be learned by practice of the invention. The following examples are provided by way of illustration, and they are not intended to be limiting of the present invention

EXAMPLES

Example 1

Preparation of N-[3-[[3-[(9-acridinecarbonyl)amino]propyl]methylamino]propyl]-10H-indolo[3,2-b]quinoline-11-carboxamide (Ia)

10H-indolo[3,2-b]quinoline-11-carboxylic acid previously prepared (cf. Bierer et al., *J. Med. Chem.* 1998, vol. 41, p. 894 (0.2 g, 0.76 mmol) was dissolved in 5 ml of refluxing SOCl$_2$. After 6 hours a clear solution was obtained, and all volatiles were removed in vacuo. The crude acid chloride was suspended in 5 ml of CH$_2$C$_2$. A solution of [3-[(3-aminopropyl)methylamino]propyl]carbamic acid tert-butyl ester previously prepared (Spicer at el., *Bioorg. Med. Chem.* 2002, vol. 10, p. 19) (0.26 g, 1.1 mmol) and triethylamine (0.4 ml) in 5 ml of CH$_2$Cl$_2$ was added at room temperature, and the mixture was stirred for 14 hours. The organic phase was washed (NaHCO$_3$, brine) and dried (MgSO$_4$). Removal of the solvent and purification by chromatography on alumina (CH$_2$Cl$_2$, MeOH, 90:10) yielded [2-[[2-[(10H-Indolo[3,2-b]quinoline-11-carbonyl)amino]ethyl]methylamino)ethyl]carbamic acid tert-butyl ester (0.26 g, 70%) as a viscous oil. $^1$H-NMR [MeOD, _, ppm]: 8.48 (d, J=7.8 Hz, 1H), 7.25 (m, 2H), 7.64 (m, 4H), 7.35 (dd, J=8.0 Hz, 1H), 3.67 (t, J=6.9 Hz, 2H, CH$_2$NO), 3.07 (t, J=6.9 Hz, 2H, CH$_2$NHBOC), 2.56 (m, 2H, CH$_2$N(CH$_3$)), 2.43 (m, 2H, CH$_2$N(CH$_3$)), 2.26 (s, 3H, N(CH$_3$)), 1.66 (m, 4H, 2CH$_2$CN(CH$_3$)), 1.48 (s, 9H, C(CH$_3$)$_3$).

To a solution of [2-[[2-[(10H-indolo[3,2-b]quinoline-11-carbonyl)amino]-ethyl]methylamino)ethyl]-carbamic acid tert-butyl ester (0.13 g, 0.27 mmol) in CH$_2$Cl$_2$ (15 ml), was added trifluoroacetic acid (3 ml). The reaction mixture was stirred at room temperature for 16 h at which point the reaction was completed by TLC. All solvents were removed under reduced pressure to give 10H-indolo[3,2-b]quinoline-[3-[(3-aminopropyl)methylamino]propyl]-11-carboxamide (0.09 g, 92%) as an oil, which was used directly in the next reaction. $^1$H-NMR [MeOD, _, ppm]: 8.51 (d, J=7.8 Hz, 1H), 8.32 (m, 2H), 8.02 (m, 1H), 7.84 (m, 2H), 7.67 (d, J=8.0 Hz, 1H), 7.44 (m, 1H), 3.76 (t, J=6.9 Hz, 2H, CH$_2$NO), 3.31 (m, 2H, CH$_2$NH$_2$), 2.96 (s, 3H, N(CH$_3$)), 2.27 (m, 2H, CH$_2$N(CH$_3$)), 2.15 (m, 2H, CH$_2$N(CH$_3$)), 1.26 (m, 4H, 2CH$_2$CN(CH$_3$)).

9-acridinecarboxylic acid (0.036 g, 0.16 mmol) was dissolved in 3 ml of refluxing SOCl$_2$. After 6 hours a clear solution was obtained, and all volatiles were removed in vacuo. The crude acid chloride was suspended in 4 ml of CH$_2$Cl$_2$. A solution of 10H-indolo[3,2-b]quinoline-[3-[(3-aminopropyl)methyl-amino]propyl]-11-carboxamide (0.076 g, 0.19 mmol) and triethylamine (0.2 ml) in 4 ml of CH$_2$Cl$_2$ was added at room temperature, and the reaction mixture was stirred for 14 hours. The organic phase was washed (NaHCO$_3$, brine) and dried (MgSO$_4$). Removal of the solvent and purification by chromatography on alumina (CH$_2$Cl$_2$(MeOH, 95:5) yielded the desired compound (55 mg, 50%) as a solid. mp 108-110° C. $^1$H-NMR [CDCl$_3$, _, ppm]: 8.38 (m, 1H), 8.05 (m, 7H), 7.58 (m, 7H), 7.26 (m, 1H), 3.59 (m, 4H, 2CH$_2$NO), 2.55 (m, 4H, 2CH$_2$NO), 2.26 (s, 3H, N(CH$_3$)), 1.91 (m, 4H, 2CH$_2$CN(CH$_3$)); MS (EI, m/z) 595 (M$^+$+1).

Example 2

Preparation of N,N'-(4-methyl-4-azaheptamethylene)-di-(10H-indolo[3,2-biquinoline-11,11'-carboxamide (Ib)

10H-indolo[3,2-b]quinoline-11-carboxylic acid (0.02 g, 0.08 mmol) was dissolved in 2 ml of refluxing SOCl$_2$. After 6 hours a clear solution was obtained, and all volatiles were removed in vacuo. The crude acid chloride was suspended in 2 ml of CH$_2$Cl$_2$. A solution of 10H-indolo[3,2-b]quinoline-[3-[(3-aminopropyl)methylamino]propyl-11-carboxamide (0.037 g, 0.09 mmol) prepared as in Example 1, and triethylamine (0.2 ml) in 2 ml of CH$_2$Cl$_2$ was added at room temperature, and the mixture was stirred for 14 hours. The organic phase was washed (NaHCO$_3$, brine) and dried (MgSO$_4$). Removal of the solvent and purification by chromatography on alumina (CH$_2$Cl$_2$/MeOH, 95:5) yielded the desired compound (30 mg, 50%) as a solid. mp 124-126° C. $^1$H NMR [CDCl$_3$, _, ppm]: 8.47 (m, 2H), 8.17 (m, 4H), 7.59 (m, 8H), 7.25 (m, 2H), 3.65 (m, 4H, 2CH$_2$NO), 2.63 (m, 4H, 2CH$_2$NO), 2.33 (s, 3H, N(CH$_3$)), 1.99 (m, 4H, 2CH$_2$CN(CH$_3$)); MS (EI, m/z) 634 (M$^+$+1).

Example 3

Preparation of N-[3-[3-[2-[1,3-dioxo-(2,3-dihydro)-1H-benzo[de]isoquinolinyl]propyl]methylamino]propyl]-10H-indolo[3,2-b]quinoline-11-carboxamide (Ic)

1,8-naphthalic anhydride (0.18 g, 0.9 mmol) was added to a solution of [3-[(3-aminopropyl)methylamino]propyl]carbamic acid tert-butyl ester previously prepared (Spicer at el., *Bioorg. Med. Chem.* 2002, vol. 10, p. 19) (0.2 g, 0.8 mmol) in absolute ethanol (20 ml). The reaction mixture was heated at reflux overnight. Removal of the solvent and purification by chromatography on alumina (CH$_2$Cl$_2$/MeOH, 50:1) yielded [3-[[3-(1,3-dioxo-3a,9b-dihydro-1H,3H-benzo[de]isoquinolin-2-yl)propyl]methylamino]propyl]carbamic acid tert-butyl ester (0.37 g, 90%) as a foam.

¹H-NMR [CDCl₃, _, ppm]: 8.62 (m, 2H), 8.22 (m, 2H), 7.72 (m, 2H), 4.23 (m, 2H, 2CH₂NO), 3.20 (m, 2H, CH₂NH), 2.55 (m, 4H, 2(CH₂)), 2.26 (s, 3H, N(CH₃)), 1.93 (m, 2H, (CH₂)), 1.68 (m, 2H, (CH₂)), 1.48 (s, 9H, C(CH₃)₃).

To a solution of [3-[[3-(1,3-dioxo-3a,9b-dihydro-1H,3H-benzo[de]isoquinolin-2-yl)propyl]methylamino]propyl]carbamic acid tert-butyl ester (0.34 g, 0.81 mmol) in CH₂Cl₂ (24 ml) was added trifluoroacetic acid (6 ml). The reaction mixture was stirred at room temperature for 16 h at which point the reaction was completed by TLC. All solvents were removed under reduced pressure to give 2-[3-[(3-aminopropyl)methylamino]propyl]-3a,9b-dihydro-benzo[de]isoquinoline-1,3-dione (0.24 g, 92%) as an oil, which was used directly in the next reaction. ¹H-NMR [MeOD, _, ppm]: 8.64 (m, 2H), 8.54 (m, 2H), 7.92 (m, 2H), 4.45 (m, 2H, 2CH₂NO), 3.55 (m, 4H, 2CH₂), 3.33 (m, 2H, CH₂), 3.22 (s, 3H, N(CH₃)), 2.44 (m, 4H, 2(CH₂)).

10H-indolo[3,2-b]quinoline-11-carboxylic acid (0.24 g, 0.9 mmol) was dissolved in 7 ml of refluxing SOCl₂. After 6 hours a clear solution was obtained, and all volatiles were removed in vacuo. The crude acid chloride was suspended in 10 ml of CH₂Cl₂. A solution of 2-[3-[(3-aminopropyl)methyl-amino]propyl]-3a,9b-dihydro-benzo[de]isoquinoline-1,3-dione (0.24 g, 0.73 mmol) and NEt₃ (1 ml) in 10 ml of CH₂Cl₂ was added at room temperature, and the reaction mixture was stirred for 14 hours. The organic phase was washed (NaHCO₃, brine) and dried (MgSO₄). Removal of the solvent and chromatography on alumina (CH₂Cl₂/MeOH, 95:5) yielded the desired compound (0.13 g, 30%) as a solid. mp 200-204° C. ¹H-NMR [CDCl₃, _, ppm]: 8.38-8.02 (m, 7H), 7.61-7.37 (m, 7H), 3.86 (m, 4H, 2CH₂NO), 2.60 and 2.40 (m, 4H, 2CH₂NO), 2.22 (s, 3H, N(CH₃)), 1.91 and 1.61 (m, 4H, 2CH₂CN(CH₃)).

Example 4

Preparation of N-[3-[[3-[2-phenyl-4-quinolinecarbonyl]amino]propyl]methylamino]propyl]-10H-indolo[3,2-b]quinoline-11-carboxamide (Id)

Activation and coupling of 10H-indolo[3,2-b]quinoline-11-carboxylic acid with 2-phenyl-quinoline-[3-[(3-aminopropyl)methylamino]propyl]-4-carboxamide (prepared analogously to Example 1 from 2-phenyl-4-quinolinecarboxylic acid), gave the desired compound as a solid, 36%, mp 144-148° C. ¹H-NMR [MeOD, _, ppm]: 8.18 (m, 2H), 8.08 (m, 4H), 7.61-7.44 (m, 10H), 7.28 (m, 1H), 3.68 (m, 2H, 2CH₂NO), 3.54 (m, 2H, 2CH₂NO), 3.34 (s, 3H, N(CH₃)), 2.64 (m, 4H, 2CH₂CN(CH₃)); 1.98 (m, 4H, 2CH₂); MS (EI, m/z) 619 (M⁺−1).

Example 5

Preparation of N,N'-(3.7-dimethyl-3.7-diazanonamethylene)di-(10H-indolo[3,2-b]quinoline-11,11'-carboxamide) (Ie)

10H-indolo[3,2-b]quinoline-11-carboxylic acid (0.25 g, 0.95 mmol) was dissolved in 5 ml of refluxing SOCl₂. After 6 hours a clear solution was obtained, and all volatiles were removed in vacuo. The crude acid chloride was suspended in 5 ml of CH₂Cl₂. A solution of [2-[[3-[(2-aminoethyl) methylamino]propyl]methylamino]ethyl]carbamic acid tert-butyl ester (Deady et al., *Bioorg. Med. Chem.* 2000, vol. 8, p. 977) (0.38 g, 1.3 mmol) and triethylamine (0.4 ml) in 5 ml of CH₂Cl₂ was added at room temperature. The reaction mixture was stirred for 14 hours. The organic phase was washed (NaHCO₃, brine) and dried (MgSO₄). Removal of the solvent and purification by chromatography on alumina (CH₂Cl₂/MeOH, 90:10) yielded [2-[[3-[[2-[(10H-indolo[3,2-b]quinoline-11-carbonyl)-amino]ethyl]methylamino]propyl]methyl-amino]ethyl]carbamic acid tert-butyl ester (0.31 g, 62%) as a viscous oil. ¹H-NMR [CDCl₃, _, ppm]: 8.45 (d, J=7.8 Hz, 1H), 8.25 (m, 2H), 7.62 (m, 4H), 7.35 (dd, J=8.0, 8.0 Hz, 1H), 3.85 (m, 2H, CH₂NO), 3.21 (m, 2H, CH₂), 3.07 (m, 2H, CH₂NHBOC), 2.79 (m, 4H, 2CH₂N(CH₃)), 2.37-2.19 (m, 4H, 2(CH₂)), 2.15 (s, 6H, 2N(CH₃)), 1.48 (s, 9H, C(CH₃)₃).

To a solution [2-[[3-[[2-[(10H-indolo[3,2-b]quinoline-11-carbonyl)amino]ethyl]methylamino]propyl]methylamino]ethyl]carbamic acid tert-butyl ester (0.3 g, 0.57 mmol) in CH₂Cl₂ (20 ml), was added trifluoroacetic acid (6 ml). The reaction mixture was stirred at room temperature for 16 h, at which point the reaction was completed by TLC. All solvents were removed under reduced pressure to give 10H-indolo[3,2-b]quinoline-[2-[[3-[(2-aminoethyl) methylamino]propyl]methylamino]ethyl]-11-carboxamide (0.23 g, 92%) as a oil, which was used directly. ¹H-NMR [MeOD, _, ppm]: 8.59 (d, J=7.8 Hz, 1H), 8.44 (m, 2H), 8.09 (m, 1H), 7.94 (m, 2H), 7.87 (d, J=8.0 Hz, 1H), 7.51 (m, 1H), 3.68 (m, 2H, CH₂NO), 3.46 (m, 8H, 4CH₂), 3.11 (m, 4H, 2CH₂N(CH₃)), 2.97 (s, 6H, 2N(CH₃)).

10H-indolo[3,2-b]quinoline-11-carboxylic acid (0.11 g, 0.41 mmol) was dissolved in 10 ml of refluxing SOCl₂. After 6 hours a clear solution was obtained, and all volatiles were removed in vacuo. The crude acid chloride was suspended in 15 ml of CH₂Cl₂. A solution of 10H-indolo[3,2-b]quinoline-11-carboxylic acid [2-[[3-[(2-aminoethyl)methylamino]propyl]methylamino]-ethyl]-amide (0.23 g, 0.5 mmol) and triethylamine (0.5 ml) in 15 ml of CH₂Cl₂ was added at room temperature. The reaction mixture was stirred for 14 hours. The organic phase was washed (NaHCO₃, brine) and dried (MgSO₄). Removal of the solvent and purification by chromatography on alumina (CH₂Cl₂/MeOH, 95:5) yielded the desired compound (0.14 g, 52%) as a foam.

¹H-NMR [CDCl₃, _, ppm]: 8.48 (m, 2H), 8.30 (m, 4H), 7.73-7.54 (m, 8H), 7.25 (m, 2H) 3.77 (m, 4H, 2CH₂NO), 2.58 (m, 4H, 2CH₂N(CH₃)), 2.38 (m, 6H, 4CH₂), 2.15 (s, 6H, 2N(CH₃)).

Example 6

Preparation of N-[(9-acridinecarbonyl)-3,7,10-triaza-3,7-dimethyldecyl]-10H-indolo[3,2-b]quinoline-11-carboxamide (If)

9-acridinecarboxylic acid (0.15 g, 0.67 mmol) was dissolved in 15 ml of refluxing SOCl₂. After 6 hours a clear solution was obtained, and all volatiles were removed in vacuo. The crude acid chloride was suspended in 15 ml of CH₂Cl₂. A solution of 10H-indolo[3,2-b]quinoline-[2-[[3-[(2-aminoethyl)methylamino]propyl]methylamino] ethyl]-11-carboxamide (0.4 g, 0.92 mmol) and triethylamine (1 ml) in 15 ml of CH₂Cl₂ was added at room temperature. The reaction mixture was stirred for 14 hours. The organic phase was washed (NaHCO₃, brine) and dried (MgSO₄). Removal of the solvent and purification by chromatography on alumina (CH₂Cl₂/MeOH, 95:5) yielded the desired compound (0.38 g, 88%) as a foam. ¹H-NMR [CDCl₃, _, ppm]: 8.12 (m, 1H), 8.02 (m, 7H), 7.58 (m, 7H), 7.33 (m, 1H), 3.77

(m, 4H, 2CH$_2$NO), 2.58 (m, 4H, 2CH$_2$N(CH$_3$)), 2.48 (m, 6H, 4CH$_2$), 2.28 (s, 6H, 2N(CH$_3$)).

Example 7

Preparation of N,N'-(3,6-dimethyl-3,6-diazaoctamethylene)-di-(10H-indolo[3,2-b]quinoline-11-11'-carboxamide (Ig)

Activation and coupling of 10H-indolo[3,2-b]quinoline-11-carboxylic acid with 10H-indolo[3,2-b]quinoline-[2-[[2-[(2-aminoethyl)methylamino]-ethyl]-methylamino]ethyl]-11-carboxamide (prepared analogously to Example 5 from [2-[[2-[(2-aminoethyl)methylamino]ethyl]methylamino]ethyl]carbamic acid tert-butyl ester) gave the desired compound as a foam, 38%. $^1$H-NMR [CDCl$_3$, —, ppm]: 8.46 (m, 2H), 8.30 (m, 4H), 7.73-7.54 (m, 8H), 7.18 (m, 2H) 3.62 (m, 4H, 2CH$_2$NO), 2.58 (m, 4H, 2CH$_2$N(CH$_3$)), 2.38 (m, 4H, 4CH$_2$), 2.35 (s, 6H, 2N(CH$_3$)).

Example 8

Preparation of N-[(9-acridinecarbonyl)-3,6-dimethyl-3,6-diazaoctamethylene)-10H-indolo[3,2-b]quinoline-11-carboxamide (Ih)

Activation and coupling of 9-acridinecarboxylic acid with 10H-indolo[3,2-b]quinoline-[2-[[2-[(2-aminoethyl)methylamino]ethyl]methylamino]ethyl]-11-carboxamide (prepared analogously to Example 5 from [2-[[2-[(2-aminoethyl)methylamino]ethyl]methylamino]ethyl] carbamic acid tert-butyl ester) gave the desired compound as a foam, 48%. $^1$H-NMR [CDCl$_3$, —, ppm]: 8.12 (m, 1H), 8.02 (m, 7H), 7.58 (m, 7H), 7.33 (m, 1H), 4.02 (m, 4H, 2CH$_2$NO), 3.98 (m, 4H, 2CH$_2$N(CH$_3$)), 3.01 (m, 4H, 4CH$_2$, 2.70 (s, 6H, 2N(CH$_3$)).

Example 9

Preparation of N-[[1,3-dioxo-(2,3-dihydro)-1H-benzo[de]isoquinolyl]-3,6-dimethyl-3,6-diazaoctamethylene]-10H-indolo[3,2-b]quinoline-11-carboxamide (Ii)

Activation and coupling of 10H-indolo[3,2-b]quinoline-11-carboxylic acid with 2-[2-[[2-[(2-aminoethyl)methylamino]ethyl]methylamino]ethyl]-benzo[de]isoquinoline-1,3-dione (prepared analogously to Example 3 from 2-[[2-[(2-amino-ethyl)methylamino]ethyl] methylamino]ethyl]carbamic acid tert-butyl ester) gave the desired compound as a foam, 37%, $^1$H-NMR [CDCl$_3$, —, ppm]: 8.55-8.11 (m, 7H), 7.72-7.17 (m, 7H), 4.03 (m, 4H, 2CH$_2$NO), 3.80 (m, 4H, 2CH$_2$N(CH$_3$)), 2.93-2.64 (m, 4H, 4CH$_2$), 2.55 (s, 6H, 2N(CH$_3$)).

Example 10

Preparation of N-[[1,3-dioxo-(2,3-dihydro)-1H-benzo[de]isoquinolyl]-3,7,10-triaza-3,7-dimethyldecyl]-10H-indolo[3,2-b]quinoline-11-carboxamide (Ij)

Activation and coupling of 10H-indolo[3,2-b]quinoline-11-carboxylic acid with 2-[2-[[3-[(2-aminoethyl)methylamino]propyl]methylamino]ethyl]-benzo[de]isoquinoline-1,3-dione (prepared analogously to Example 3 from 2-[[3-[(2-aminoethyl)methylamino]propyl-methylamino]ethyl]carbamic acid tert-butyl ester) gave the desired compound as a foam, 40%. $^1$H-NMR [CDCl$_3$, —, ppm]: 8.59-8.02 (m, 7H), 7.77-7.25 (m, 7H), 4.05 (m, 4H, 2CH$_2$NO), 3.82 (m, 4H, 2CH$_2$N(CH$_3$)), 2.78-2.34 (m, 6H, 4CH$_2$), 2.25 (s, 6H, 2N(CH$_3$)).

Example 11

Preparation of 5-methyl-5H-indolo[3,2-b]quinoline-11-Carboxylic Acid Intermediate for the Preparation of (Im)

The 5-methyl-5H-indolo[3,2-b]quinoline-11-carboxylic acid is known in the literature as part of extract plant *Cryptolepis sanguinolenta* (cf. Paulo et al., *Planta Medica* 2000, vol. 66, p. 30). It can also be prepared by the following process:

5,11-dimethyl-5H-indolo[3,2-b]quinoline (cf. Yang et al., *J. Nat. Prod*, 1999, vol. 62, pp. 976] (0.1 g, 0.4 mmol) was added to 10 ml of water. KMnO$_4$ (64 mg. 0.4 mmol) is added, and the solution is heated to reflux for 1 h. Then a second portion of KMnO$_4$ (64 mg. 0.4 mmol) is introduced, followed by 10 ml of water, and the heating is continued for 1 h. The reaction mixture is allowed to cool slightly, and the precipitated oxide of manganese is filtered and washed with hot water. The filtrated is concentrated under reduced pressure to half of the volume, filtered and acidified with concentrated hydrochloric acid. This acid solution is then evaporated to dryness under reduced pressure to give the desired compound (70 mg, 64%), which was used directly. $^1$H-NMR [MeOD, ppm]: 8.24 (m, 2H), 7.79 (m, 2H), 7.54 (m, 4H), 5.15 (s, 3H) MS (EI, ml) 277 (M$^+$+1).

Example 12

Preparation of N,N'-(4-methyl-4-azaheptamethylene)-di-(5-methyl-5H-indolo[3,2-b]quinoline-11,11'-carboxamide) (Im)

Activation and coupling of 5-methyl-5H-indolo[3,2-b]quinoline-11-carboxylic acid, prepared as in Example 11, with 5-methyl-5H-indolo[3,2-b]quinoline-[3-[(3-aminopropyl)methylamino]propyl]-11 carboxamide (prepared analogously to Example 1 from 5-methyl-5H-indolo[3,2-b]quinoline-11-carboxylic acid) gave the desired compound as a foam, 50%, $^1$HNMR [CDCl$_3$, —, ppm]: 8.47 (m, 2H), 8.17 (m, 4H), 7.59 (m, 8H), 7.25 (m, 2H), 5.15 (s, 6H), 3.65 (m, 4H, 2CH$_2$NO), 2.63 (m, 4H, 2CH$_2$NO), 2.33 (s, 3H, N(CH$_3$)), 1.99 (m, 4H, 2CH$_2$CN(CH$_3$)).

Example 13

Preparation of 10H-indolo[3,2-b]quinoline-11-carbonyl-glicine-arginine (Io)

The compound of the title was prepared by solid phase methods. After assembling the Boc-glicine-arginine sequence on a p-methylbenzhydrylamine resin, the N-terminal was deprotected and 10H-indolo[3,2-b]quinoline-11-carboxylic acid was coupled by means of benzotriazol-1-yloxytripyrrolidinophosphonium hexafluoro-phosphate (PyBOP) and diisopropylethylamine (5, 5 and 10 equivalents, respectively) in 1:1 DMSO-DMF for 1 h. Acidolysis with HF/anisole (9:1, 0° C., 1 h) provided the desired compound in highly homogeneous form (>98% by HPLC). MS(MALDI-TOF): EM(expected): 474.1; EM(found): 475.5 (M+H⁺).

Example 14

Preparation of N,N-dimethyl-N'-(5-methyl-5H-indolo[3,2-b]quinolin-11-yl)-ethane-1,2-diamine (Ip)

A solution of 11-cloro-5-metil-5$\underline{H}$-indolo[3,2-b]quinoline previously prepared (cf. Bierer et al., *J. Med. Chem.* 1998, vol. 41, p. 2754) (66 mg, 0.25 mmol) and N,N-dimethylethylenediamine (94_l, 1 mmol) in 2-ethoxyethanol (10 ml) was heated at 120° C. for 10 min. Removal of the solvent and chromatography on alumina (CHCl₃ 100%) yielded the desired compound (36 mg, 46%) as a yellow solid. m. p. 162-164° C. ¹H NMR [CDCl₃_, ppm]: 8.28 (d, J=8.5 Hz, 1H), 7.89 (m, 2H), 7.69-7.61 (m, 3H), 7.31 (m, 2H), 4.58 (s, 3H, NCH₃), 4.32 (m, 2H, CH₂), 3.14 (m, 2H, CH₂), 2.51 (s, 6H, N(CH₃)₂).

Example 15

Preparation of N,N'-(4-methyl-4-azaheptamethylen)-di-(5-methyl-5H-indolo[3,2-b]quinoline-11,11'-amine (Iq)

A solution of 11-chloro-5-methyl-5$\underline{H}$-indolo[3,2-b]quinoline (cf. Bierer et al., *J. Med. Chem.* 1998, vol. 41, pp. 2754) (61 mg, 0.23 mmol) and [[3-[(3-amino-propyl)methylamino]propyl]carbamic acid tert-butyl ester previously prepared (Spicer et el., *Bioorg. Med. Chem.* 2002, vol. 10, p. 19) (84_l, 0.34 mmol) in 2-ethoxyethanol (10 ml) was heated at 120° C. for 10 min. Removal of the solvent and purification by chromatography on alumina (CHCl₃: MeOH 2%) yielded [3-[methyl-[3-(5-methyl-5$\underline{H}$-indolo[3,2-b]quinolin-11-yl-amino)propyl]-amino] propyl]carbamic acid tert-butyl ester (49 mg, 490%) as a foam. ¹H NMR [CDCl₃_, ppm]: 8.16 (d, J=8.5 Hz, 1H), 7.81 (m, 4H), 7.55-7.48 (m, 2H), 7.21 (m, 1H), 4.51 (s, 3H, NCH₃), 4.27 (m, 2H, CH₂NO), 3.12 (m, 2H, CH₂NHBOC), 2.76 (m, 2H, CH₂N(CH₃)), 2.63 (m, 2H, CH₂N(CH₃)), 2.39 (s, 3H, N(CH₃)), 2.34 (m, 2H, CH₂CN(CH₃)), 1.73 (m, 2H, CH₂CN(CH₃)), 1.37 (s, 9H, C(CH₃)₃).

To a solution of [3-[methyl-[3-(5-methyl-5$\underline{H}$-indolo[3,2-b]quinolin-11-ylamino)-propyl]amino] propyl)-carbamic acid tert-butyl ester (49 mg, 0.1 mmol) in CH₂Cl₂ (10 ml), was added trifluoroacetic acid (12_l). This mixture was stirred at room temperature for 16 h, at which point the reaction was completed by TLC. All solvents were removed under reduced pressure to give N¹-methyl-N¹-[3-(5-methyl-5$\underline{H}$-indolo[3,2-b]quinolin-11-ylamino)propyl]propane-1,3-diamine (38 mg, 92%) as an oil, which was used directly. ¹H-NMR [MeOD,_, ppm]: 8.52 (d, J=8.5 Hz, 1H), 8.35-7.73 (m, 4H), 7.63-7.60 (m, 2H), 7.31 (m, 1H), 4.45 (s, 3H, NCH₃), 3.60 (m, 2H, CH₂NO), 3.02 (m, 2H, CH₂N(CH₃)), 2.92 (s, 3H, N(CH₃)), 2.36 (m, 4H, 2CH₂CN(CH₃)), 2.14 (m, 2H, CH₂N(CH₃)), 1.90 (m, 2H, CH₂CN(CH₃)).

A solution of 11-chloro-5-methyl-5$\underline{H}$-indolo[3,2-b]quinoline, previously prepared, (cf. Bierer et al., *J. Med. Chem.* 1998, vol. 41, p. 2754) (40 mg, 0.15 mmol) and N¹-methyl-N¹-[3-(5-methyl-5$\underline{H}$-indolo[3,2-b]quinolin-11-ylamino)-propyl]propane-1,3-diamine (38 mg, 0.1 mmol) in 2-ethoxyethanol (10 ml) was heated at 120° C. for 10 min. Removal of the solvent and purification by chromatography on alumina (CHCl₃ 100%) yielded the desired compound (17 mg, 46%) as a foam. ¹H NMR [CDCl₃_, ppm]: 8.16-8.21 (m, 4H), 8.01 (m, 2H), 7.93-7.71 (m, 4H), 7.50-7.30 (m, 2H), 7.23-7.25 (m, 4H), 4.26 (s, 3H, NCH₃), 4.24 (s, 3H, NCH₃), 4.12 (m, 2H, CH₂NO), 3.03 (m, 2H, CH₂), 2.80 (m, 2H, CH₂N(CH₃)), 2.70 (m, 2H, CH₂N (CH₃)), 2.44 (s, 3H, N(CH₃)), 2.16 (m, 2H, CH₂CN(CH₃)), 1.72 (m, 2H, CH₂CN(CH₃)).

Example 16

Preparation of N-1-[5-hydroxymethyl-6-(5'-TTCCG-GAA-3'-phosphate)-hexyl]-10H-indolo[3,2-b]quinoline-11-carboxamide by Solid Phase Coupling (Ir)

5'TTCCGGAA-NH₂-3' oligonucleotide sequence carrying an amino group at the 3' end was prepared using 3-O-dimethoxytrityloxy-2-(N-9-fluorenphenylmethoxycarbonyl-4-aminobutyl)-1-propanyl ester succinamidyl-controlled pore glass (3'amino C7 modifier CPG from Glen Research). The solid support obtained after the assembly of the sequence was treated with a 0.1 M solution of 1,8-diazabiciclo[5.4.0] undece-7-ene (DBU) in dry acetonitrile (2 min, room temperature). In this way, the Fmoc group that protects the amino group is removed selectively with a non-nucleophillic base. The resulting support was washed with acetonitrile and reacted with 10$\underline{H}$-indolo[3,2-b]quinoline-11-carboxylic acid as follows. A mixture containing 10 molar excess of 10 $\underline{H}$-indolo[3,2-b]quinoline-11-carboxylic acid, 20 molar excess of diisopropylethylamine (DIEA) as base catalyst and 10 molar excess of (benzotriazol-1-yloxy) trispyrrolidino-phosphonium hexafluorophosphate (PyBOP) as carboxyl activator was prepared in dry dimethylformamide (DMF) (0.2 ml). The mixture was left for 2 min at room temperature and added to the support. After 1 hour at room temperature, the mixture was filtered and washed with DMF. The support was dried and concentrated ammonia (1 ml) was added. The ammonia solution was left for 1 hr at 50° C. The mixture was filtered and the ammonia solution was concentrated to dryness. The residue was dissolved in water and desalted by NAP-10 (Sephadex G-25) eluted with water. Finally, the oligonucleotide fractions were analyzed by HPLC. HPLC solutions were as follows. Solvent A: 5% ACN in 100 mM triethylammonium acetate pH 6.5 and solvent B: 70% ACN in 100 mM triethylammonium acetate pH 6.5. Columns: PRP-1 (Hamilton), 250×10 mm. Flow rate: 3 ml/min. A 20 min linear gradient from 5-35%. The compound of the title eluted at 14.0 min. Unreacted amino-oligonucleotide eluted around 9 min. The desired product was characterized by the UV-spectra. UVmax: 258,348. Yield: 7%.

Example 17

Preparation of N-1-[5-hydroxymethyl-6-(5'-TTCCG-GAA-3'-phosphate)-hexyl]-10H-indolo[3,2-b]quinoline-11-carboxamide by Solution-Phase Coupling (Ir)

5'TTCCGGAA-NH₂ 3' oligonucleotide sequence carrying an amino group at the 3' end was prepared using the 3'amino C7 modifier CPG (Glen Research). The solid support obtained after the assembly of the sequence was treated with concentrated ammonia for 1 hr at 50° C. The mixture was filtered and the ammonia solution was concentrated to dryness. The residue was passed over a Dowex 50×4 (Na+ form) column to exchange ammonium ions for sodium ions. The resulting amino-oligonucleotide was dissolved in 0.1 ml of water, and mixed with 0.1 ml of 1 M sodium carbonate aqueous buffer pH 8-9. In a separate container 10 H-indolo[3,2-b]quinoline-11-carboxylic acid (10 molar excess) was dissolved in 0.1 ml of DMF, and mixed with N-hydroxysuccinimide (10 molar excess) and N,N-diisopropylcarbodiimide (10 molar excess). The mixture was left for 10 min at room temperature and added to the aqueous solution of the amino-oligonucleotide. The reaction mixture was kept at room temperature overnight. The mixture was concentrated to dryness and the residue was dissolved in water. The solution was passed through a NAP-10 column. The fractions containing oligonucleotide were analyzed by HPLC. HPLC solutions were as follows: Solvent A: 5% ACN in 100 mM triethylammonium acetate pH 6.5 and solvent B: 70% ACN in 100 mM triethylammonium acetate pH 6.5. Columns: PRP-1 (Hamilton), 250×10 mm. Flow rate: 3 ml/min. A 20 min linear gradient from 5-35%. The compound of the title eluted at 14.0 min Unreacted amino-oligonucleotide eluted around 9 min. The desired product was characterized by the UV-spectra. UVmax: 258, 348 and mass spectrometry (MALDI-TOF): found 2861 (M+H$^+$) expected 2862. Yield: 18%.

Example 18

Preparation of N-1-[5-hydroxymethyl-6-(5'-CTTC-CTCCTCT-3'-phosphate)-hexyl]-10H-indolo[3,2-b]quinoline-11-carboxamide by Solid Phase Coupling (Is)

The compound of the title was obtained in a similar way to example 16 but ammonia treatment was run for 2 hours at room temperature. The compound of the title eluted at 13.8 min. It was characterized by the UV-spectra. UVmax: 273, 349. Yield: 5%.

Example 19

Preparation of N-1-[5-hydroxymethyl-6-(5'-CTTC-CTCCTCT-3'-phosphate)-hexyl]-10H-indolo[3,2-b]quinoline-11-carboxamide by Solution-Phase Coupling (Is)

The compound of the title was obtained in a similar way to example 17. The compound of the title eluted at 13.9 min. It was characterized by the UV-spectra. UVmax: 273, 349, and mass spectrometry (MALDI-TOF): found 3646 (M+H$^+$) expected 3647. Yield: 20%.

Example 20

Preparation of N-1-[6-(5'-phosphate-TTCCGGAA)-hexyl]-10H-indolo[3,2-b]quinoline-11-carboxamide by Solution-Phase Coupling (It)

5'NH$_2$-TTCCGGAA 3' oligonucleotide sequence carrying an amino group at the 5' end was prepared using the phosphoramidite of the N6-monomethoxytrityl (MMT) protected derivative of 6-aminohexanol (Glen Research). The solid support obtained after the assembly of the sequence was treated with concentrated ammonia for 1 hr at 50° C. Reaction of the 5' amino-oligonucleotide with 10 H-indolo[3,2-b]quinoline-11-carboxylic acid was carried out as described in example 17. The compound of the title eluted at 16 min. The desired product was characterized by the UV-spectra UVmax: 268, 349. Yield: 12%.

Example 21

Preparation of 10H-indolo[3,2-b]quinoline-11-carboxylic acid (2-dimethylamino-ethyl)amide (Iu)

10H-indolo[3,2-b]quinoline-11-carboxylic acid (0.5 g, 1.9 mmol) was dissolved in 20 ml of refluxing SOCl$_2$, After 6 hours a clear solution was obtained, and all volatiles were removed in vacuo. The crude acid chloride was suspended in 10 ml of CH$_2$Cl$_2$. A solution of N,N-dimethylethylendiamine (0.2 mL, 2.26 mmol) and triethylamine (2.2 ml) in 10 ml of CH$_2$Cl$_2$ was added at room temperature, and the mixture was stirred for 14 hours. The organic phase was washed (NaHCO$_3$, brine) and dried (MgSO$_4$). Removal of the solvent and purification by chromatography on alumina (CH$_2$Cl$_2$/MeOH, 90:10) yielded the desired compound (0.38 g, 61%) as a solid. m. p. 175-176° C. $^1$H-NMR [MeOD, _, ppm]: 8.16 (d, J=7.8 Hz, 1H), 7.92 (m, 2H), 7.35-7.20 (m, 3H), 7.04 (m, 2H), 3.62 (m, 2H, CH$_2$NO), 2.55 (m, 2H, CH$_2$N(CH$_3$)$_2$), 2.29 (s, 6H, N(CH$_3$)$_j$. MS (EI, m/z) 277 (M$^+$+1).

Example 22

Preparation of 10H-Indolo[3,2-b]quinoline-11-carboxylic acid (2-dimethylamino-propyl)amide (Iv)

10H-Indolo[3,2-b]quinoline-11-carboxylic acid (0.2 g, 0.76 mmol) was dissolved in 8 ml of refluxing SOCl$_2$. After 6 hours a clear solution was obtained, and all volatiles were removed in vacuo. The crude acid chloride was suspended in 10 ml of CH$_2$Cl$_2$. A solution of N,N-dimethylproylendiamine (0.1 mL, 0.97 mmol) and triethylamine (1 ml) in 10 ml of CH$_2$Cl$_2$ was added at room temperature, and the mixture was stirred for 14 hours. The organic phase was washed (NaHCO$_3$, brine) and dried (MgSO$_4$). Removal of the solvent and purification by chromatography on alumina (CH$_2$Cl$_2$/MeOH, 90:10) yielded the desired compound (80 mg, 31%) as a solid. m. p. 188-189° C. $^1$H-NMR [MeOD,_, ppm]: 8.16 (d, J=7.8 Hz, 1H), 7.92 (m, 2H), 7.35-7.20 (m, 3H), 7.04 (m, 2H), 3.62 (m, 2H, CH$_2$NO), 2.55 (m, 2H, CH$_2$N(CH$_3$)$_2$), 2.29 (s, 6H, N(CH$_3$)$_2$), 1.88 (m, 2H, CHO. MS (EI, m/z) 347 (M$^+$+1).

Example 23

Preparation of N,N-dimethyl-N'-(5-methyl-5H-indolo[3,2-b]quinolin-11-yl)-propane-1,2-diamine (Iw)

A solution of 11-chloro-5-metil-5 H-indolo[3,2-b]quinoline (47 mg, 0.17 mmol) and N,N-dimethylpropylenediamine (78_l, 0.76 mmol) in 2-ethoxyethanol (5 ml) was heated at 120° C. for 10 min. Removal of the solvent and chromatography on alumina (CHCl$_3$ 100%) yielded the desired compound (20 mg, 35%) as a foam. $^1$H NMR [CDCl$_3$_, ppm]: 8.28 (d, J=8.5 Hz, 1H), 7.89 (m, 2H), 7.69-7.61 (m, 3H), 7.31 (m, 2H), 4.58 (s, 3H, NCH$_3$), 4.23 (m, 2H, CH$_2$), 3.86 (m, 2H, CH$_2$), 3.55 (m, 2H, CH$_2$), 2.55 (s, 6H, N(CH$_3$)$_2$). MS (EI, m/z) 333 (M$^+$+1).

Example 24

Preparation of N-[3-[[3-[(10H-indolo[3,2-b]quinoline-4-carboxamide]propyl]methylamino]propyl]-10H-indolo[3,2-b]quinoline-11-carboxamide (Ix)

10H-indolo[3,2-b]quinoline-4-carboxylic acid (0.2 g, 0.76 mmol) was dissolved in 5 ml of refluxing $SOCl_2$. After 6 hours a clear solution was obtained, and all volatiles were removed in vacuo. The crude acid chloride was suspended in 5 ml of $CH_2Cl_2$. A solution of [3-[(3-aminopropyl)methylamino]propyl]carbamic acid tert-butyl ester (0.26 g, 1.1 mmol) and triethylamine (0.4 ml) in 5 ml of $CH_2Cl_2$ was added at room temperature, and the mixture was stirred for 14 hours. The organic phase was washed ($NaHCO_3$, brine, HCl 1 N) and dried ($MgSO_4$). All solvents were removed under reduced pressure to give 10H-indolo[3,2-b]quinoline-[3-[(3-aminopropyl)methylamino]propyl]-4-carboxamide (0.14 g, 48%) as an oil, which was used directly in the next reaction. $^1$H-NMR [MeOD, _, ppm]: 8.72 (d, J=7.8 Hz, 1H), 8.63 (d, J=7.8 Hz, 1H), 8.51 (d, J=7.8 Hz, 1H), 7.97 (m, 2H), 7.79 (d, J=8.0 Hz, 1H), 7.43 (m, 2H), 3.75 (t, J=6.9 Hz, 2H, $CH_2NO$), 3.31 (m, 2H, $CH_2NH_2$), 2.96 (s, 3H, $N(CH_3)$), 2.27 (m, 2H, $CH_2N(CH_3)$), 2.15 (m, 2H, $CH_2N(CH_3)$), 1.35 (m, 4H, $2CH_2CN(CH_3)$).

10H-indolo[3,2-b]quinoline-11-carboxylic acid (0.066 g, 0.25 mmol) was dissolved in 3 ml of refluxing $SOCl_2$. After 6 hours a clear solution was obtained, and all volatiles were removed in vacuo. The crude acid chloride was suspended in 2 ml of $CH_2Cl_2$. A solution of 10H-indolo[3,2-b]quinoline-[3-[(3-aminopropyl)methyl-amino]propyl]-4-carboxamide (0.14 g, 0.36 mmol) and triethylamine (0.2 ml) in 2 ml of $CH_2Cl_2$ was added at room temperature, and the reaction mixture was stirred for 14 hours. The organic phase was washed ($NaHCO_3$, brine) and dried ($MgSO_4$). Removal of the solvent and purification by chromatography on alumina ($CH_2Cl_2$/MeOH, 95:5) yielded the desired compound (27 mg, 17%) as an oil. $^1$H-NMR [CDCl3, _, ppm]: 8.43 (m, 1H), 8.28 (m, 7H), 7.58 (m, 7H), 7.26 (m, 1H), 3.20 (m, 4H, $2CH_2NO$), 2.49 (m, 4H, $2CH_2NO$), 2.05 (s, 3H, $N(CH_3)$), 1.64 (m, 4H, $2CH_2CN(CH_3)$).

Example 25

Preparation of N,N'-(3,7-dimethyl-3,7-diazanonamethylene)-di-(5-methyl-5H-indolo[3,2-b]quinoline-11,11'-carboxamide) (Iy)

Activation and coupling of 5-methyl-5H-indolo[3,2-b]quinoline-11-carboxylic acid with 5-methyl-5H-indolo[3,2-b]quinoline[2-[[2-[(2-aminoethyl)methylamino]-ethyl]-methylamino]ethyl]-11-carboxamide (prepared analogously to Example 5 from [2-[[3-[(2-aminoethyl)methylamino]propyl] methylamino]ethyl]carbamic acid tert-butyl ester and 5-methyl-5H-indolo[3,2-b]quinoline-11-carboxylic acid gave the desired compound as a foam, (4 mg, 15%), $^1$H NMR [CDCl3_, ppm]: 8.47 (m, 2H), 8.17 (m, 4H), 7.59 (m, 8H), 7.25 (m, 2H), 5.15 (s, 6H), 3.77 (m, 4H, $2CH_2NO$), 2.58 (m, 4H, $2CH_2N(CH_3)$), 2.38 (m, 6H, $4CH_2$), 2.15 (s, 6H, $2N(CH_3)$).

Example 26

Preparation of N,N'-(3,6-dimethyl-3,6-diazaoctamethylene)-di-(5-methyl-5H-indolo[3,2-b]quinolin-11,11-carboxamide) (Iz)

Activation and coupling of 5-methyl-5H-indolo[3,2-b]quinoline-11-carboxylic acid with 5-methyl-5H-indolo[3,2-b]quinoline[2-[[2-[(2-aminoethyl)methylamino]-ethyl]-methyl-amino]ethyl]-11-carboxamide (prepared analogously to Example 7 from [2-[12-[(2-aminoethyl)methylamino]ethyl] methylamino]ethyl]carbamic acid tert-butyl ester and 5-methyl-5H-indolo[3,2-b]quinoline-11-carboxylic acid gave the desired compound as a foam, (28 mg, 10%), $^1$H NMR [CDCl3, ppm]: 8.47 (m, 2H), 8.17 (m, 4H), 7.59 (m, 8H), 7.25 (m, 2H), 5.15 (s, 6H), 3.65 (m, 4H, $2CH_2NO$), 2.58 (m, 4H, $2CH_2N(CH_3)$), 2.38 (m, 4H, $4CH_2$), 2.35 (s, 6H, $2N(CH_3)$).

Example 27

Preparation of (3,7-diazanonamethylene)-di-(10H-indolo[3,2-b]quinoline-11,11'-carboxamide (Iaa)

10H-indolo[3,2-b]quinoline-11-carboxylic acid (0.056 g, 0.21 mmol) was dissolved in 2 ml of refluxing $SOCl_2$. After 6 hours a clear solution was obtained, and all volatiles were removed in vacuo. The crude acid chloride was suspended in 2 ml of $CH_2Cl_2$. A solution of (2-[3-(2-amino-ethylamino]-ethyl)-carbamic acid tert-butyl ester (0.079 g, 0.3 mmol) and triethylamine (0.2 ml) in 2 ml of $CH_2Cl_2$ was added at room temperature. The reaction mixture was stirred for 14 hours. The organic phase was washed ($NaHCO_3$, brine) and dried ($MgSO_4$). Removal of the solvent and purification by chromatography on alumina ($CH_2Cl_2$/MeOH, 90:10) yielded [2-(342-[10H-indolo[3,2-b]quinoline-11-carbonyl)-amino]-ethylamino)propylamino)-ethyl]carbamic acid tert-butyl ester (0.025 g, 25%) as a viscous oil. $^1$H-NMR [CDCl3, _, ppm]: 8.46 (d, J=7.8 Hz, 1H), 8.30 (m, 2H), 7.68 (m, 4H), 7.53 (dd, J=8.0, 8.0 Hz, 1H), 3.65 (m, 2H, $CH_2NO$), 3.12 (m, 2H, $CH_2$), 3.07 (m, 2H, $CH_2NHBOC$), 2.06 (m, 4H, $2CH_2NH$), 1.67-1.55 (m, 4H, $2(CH_2)$), 1.48 (s, 9H, $C(CH_3)_3$).

To a solution [2-(3-(2-[10H-indolo[3,2-b]quinoline-11-carbonyl)-amino]-ethylamino)-propylamino)-ethyl]carbamic acid tert-butyl ester (0.025 g, 0.049 mmol) in $CH_2Cl_2$ (5 ml), was added trifluoroacetic acid (1 ml). The reaction mixture was stirred at room temperature for 16 h, at which point the reaction was completed by TLC. All solvents were removed under reduced pressure to give 10H-indolo[3,2-b] quinoline-11-carboxylic acid (2-[3-(2-amino-ethylamino)-propylamino]-ethyl]-amide (0.02 g, 95%) as a oil, which was used directly. $^1$H-NMR [MeOD, _, ppm]: 8.55 (d, J=7.8 Hz, 1H), 8.26 (m, 2H), 8.00 (m, 1H), 7.80 (m, 2H), 7.64 (d, J=8.0 Hz, 1H), 7.26 (m, 1H), 4.19 (m, 2H, $CH_2NO$), 3.56 (m, 8H, $4CH_2$), 3.20 (m, 4H, $2CH_2NH$).

10H-indolo[3,2-b]quinoline-11-carboxylic acid (0.009 g, 0.034 mmol) was dissolved in 2 ml of refluxing $SOCl_2$. After 6 hours a clear solution was obtained, and all volatiles were removed in vacuo. The crude acid chloride was suspended in 2 ml of $CH_2Cl_2$. A solution of 10H-indolo[3,2-b]quinoline-11-carboxylic acid (2-[3-(2-amino-ethylamino)-propylamino]-ethyl]-amide (0.02 g, 0.049 mmol) and triethylamine (0.2 ml) in 2 ml of $CH_2Cl_2$ was added at room temperature. The reaction mixture was stirred for 14 hours. The organic phase was washed ($NaHCO_3$, brine) and dried ($MgSO_4$). Removal of the solvent and purification by chromatography on alumina ($CH_2Cl$/MeOH, 95:5) yielded the desired compound (0.015 g, 68%) as a foam. $^1$H-NMR [CDCl3, _, ppm]: 8.56 (m, 2H), 8.30 (m, 4H), 7.88-7.65 (m, 8H), 7.15 (m, 2H) 3.62 (m, 4H, $2CH_2NO$), 2.37 (m, 4H, $2CH_2NH$), 2.17 (m, 6H, $4CH_2$).

Example 28

Preparation of N,N'-(3.7-dimethyl-3,7-diazanonamethylene)-di-(5-methyl-5H-indolo[3,2-b]quinoline-11,11'-amine (Iab)

Activation and coupling of 11-chloro-5-methyl-5H-indolo [3,2-b]quinoline with N-(2-amino-ethyl)-(N,N'-dimethyl-N'-

[2-(5-methyl-5H-indolo[3,2-b]quinolin-11-ylamino)-ethyl]-propane-1,3-diamine (prepared analogously to Example 15 from [2-[[3-[(2-aminoethyl)methylamino]propyl]methylamino]ethyl]carbamic acid tert-butyl ester and 11-chloro-5-methyl-5H-indolo[3,2-b]quinoline gave the desired compound as a foam, (13 mg, 16%), $^1$H NMR [CDCl$_3$__, ppm]: 8.58-8.40 (m, 4H), 8.01 (m, 2H), 7.84-7.64 (m, 4H), 7.63-7.55 (m, 2H), 7.42-7.27 (m, 4H), 4.61 (s, 6H, NCH$_3$), 4.12 (m, 4H, 2CH$_2$NH), 2.58 (m, 4H, 2CH$_2$N(CH$_3$)), 2.38 (m, 6H, 4CH$_2$), 2.15 (s, 6H, 2N(CH$_3$)).

Example 29

Preparation of N,N'-(3,6-dimethyl-3,6-diazaoctamethylene)-di-(5-methyl-5H-indolo[3,2-b]quinoline-11,11'-amine (Iac)

Activation and coupling of 11-chloro-5-methyl-5H-indolo[3,2-b]quinoline with N-(2-amino-ethyl)-(N,N'-dimethyl-N'-[2-(5-methyl-5H-indolo[3,2-b]quinolin-11-ylamino)-ethyl]-ethane-1,2-diamine (prepared analogously to Example 15 from [2-[[2-[(2-aminoethyl)methylamino]ethyl]methylamino]ethyl]carbamic acid tert-butyl ester and 11-chloro-5-methyl-5H-indolo[3,2-b]quinoline gave the desired compound as a foam, (23 mg, 56%), $^1$H NMR [CDCl$_3$__, ppm]: 8.66-8.21 (m, 4H), 8.01 (m, 2H), 7.84-7.64 (m, 4H), 7.63-7.55 (m, 2H), 7.42-7.27 (m, 4H), 4.91 (s, 6H, NCH$_3$), 4.12 (m, 4H, 2CH$_2$NH), 2.58 (m, 4H, 2CH$_2$N(CH$_3$)), 2.38 (m, 4H, 4CH$_2$), 2.35 (s, 6H, 2N(CH$_3$)).

Example 30

In Vitro Biological Test

The in vitro cytotoxicity of the compounds of the present invention was evaluated by colorimetric assays with tetrazol salts (MTT) on Jurkat clon E6-1 and on GLC-4, human leukemia and carcinoma cell lines, respectively. This assay is based on the capacity of live cells to incorporate and reduce the MTT, with yellow colour in a red derivative. This reduction is done by the action of the mitochondrial enzyme succinate hydrogenase, only active in live cells. The intensity of observed colour is directly correlated with the quantity of live cells in the sample as it is described by Mosmann et al., *J. Immunol. Methods* 1983, vol. 65, p. 55. In all cases the concentrations used were up to 100 mikroM and times of incubation until 72 h. Table 1 shows the biological activity (IC$_{50}$) of some compounds of formula (I)

TABLE 1

Biological activities.

| Compound (I) | IC$_{50}$ (__M) Jurkat clon E6-1 | IC$_{50}$ (__M)GLC-4 |
|---|---|---|
| Ia | 1.42 | 1.63 |
| Ib | 0.59 | 1.10 |
| Ic | 0.95 | 4.70 |
| Id | 3.37 | 3.57 |
| Ie | 5.13 | 2.88 |
| If | 7.16 | 3.64 |
| Ip | 0.26 | 0.67 |
| Iu | 18.7 | 15.70 |
| Iv | Not tested | 16.73 |
| Iw | Not tested | 1.08 |
| Ix | 1.21 | 19.57 |
| Iy | 7.94 | 19.08 |
| Iz | 5.02 | 11.53 |
| Iac | Not tested | 5.88 |

The invention claimed is:

1. A compound of formula (I)

$$G_1\text{-}L\text{-}G_2 \quad (I)$$

or a pharmaceutically acceptable salt thereof, wherein:
-G$_1$ is a radical (II)

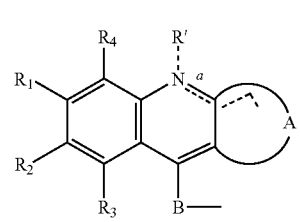

wherein —R' is an electron pair or a (C$_1$-C$_3$)-alkyl radical; with the condition that
(i) when —R' is an electron pair, a is a N═C double bond and the fused ring

is the biradical

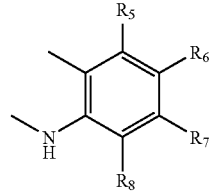

thus radical (II) is (IIa'), and

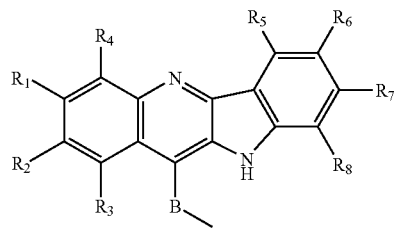

(ii) when —R' is a (C$_1$-C$_3$)-alkyl radical, a is a N—C single bond and the fused ring is the triradical

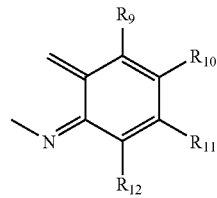

thus radical (II) is (IIa″);

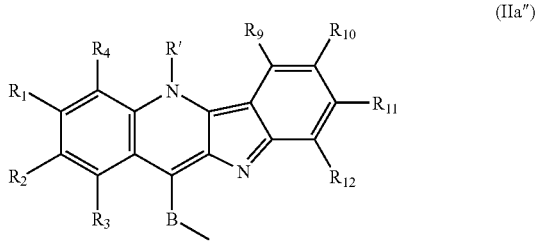
(IIa″)

wherein —R$_1$ to —R$_{12}$ represent radicals, same or different, selected from the group consisting of H, (C$_1$-C$_4$)-alkyl, (C$_1$-C$_4$)-alkoxy, (C$_1$-C$_4$)-alkylamino, phenyl, F, Cl, Br, amino, hydroxy, and nitro;

and wherein —B— is a biradical selected from the group consisting of —CONH—,

—NR$_{13}$—, —O—, —(CH$_2$)$_n$NH—, and —(CH$_2$)$_n$O—; wherein —R$_{13}$ is selected from the group consisting of H, (C$_1$-C$_4$)-alkyl, (C$_1$-C$_4$)-alkoxy and (C$_1$-C$_4$)-alkylamino; and n is an integer from 1 to 3;

-L- is a covalent linking biradical selected from the following ones;

—(CH$_2$)$_r$NR‴(CH$_2$)$_s$—

—(CH$_2$)$_r$NR‴(CH$_2$)$_s$NR″″(CH$_2$)$_t$— wherein —R‴ and —R″″ are radicals, same or different, selected from the group consisting of H and (C$_1$-C$_3$)-alkyl; r is an integer from 1 to 3; s is an integer from 1 to 3; t is an integer from 1 to 3; and -G$_2$- is a radical selected from a radical of formula (II), the N-radical of 1,8-naphthalimide, the C4-radical of 2-phenylquinoline, and the C9-radical of acridine.

2. The compound according to claim 1, wherein (II) is the radical (IIa′)

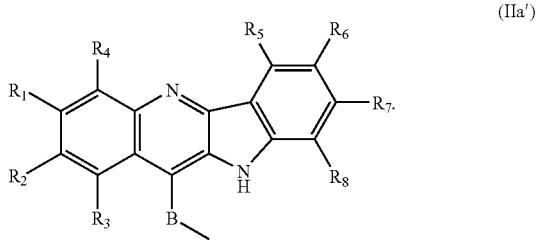
(IIa′)

3. The compound according to claim 2, wherein —B— is selected from the group consisting of —CONH— and —NR$_{13}$—.

4. The compound according to claim 2, wherein -L- is a covalent linking biradical selected from the following ones —(CH$_2$)$_r$NR‴(CH$_2$)$_s$—

—(CH$_2$)$_r$NR‴(CH$_2$)$_s$NR″″(CH$_2$)$_t$—.

5. The compound according to claim 4, wherein -L- is the biradical —(CH$_2$)$_r$NR‴(CH$_2$)$_s$—, —R‴ is methyl, and both r and s are 3.

6. The compound according to claim 4, wherein -L- is the covalent linking biradical —(CH$_2$)$_r$NR‴(CH$_2$)$_s$NR″″(CH$_2$)$_t$—, both —R‴ and —R″″ are methyl; both r and t are 2, and s is 2 or 3.

7. The compound according to claim 1, wherein (II) is the radical (IIa″)

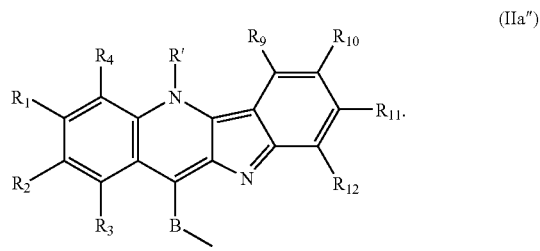
(IIa″)

8. The compound according to claim 7, wherein —B— is selected from the group consisting of —CONH— and —NR$_{13}$—.

9. The compound according to claim 7, wherein —R′ is methyl.

10. The compound according to claim 9, wherein -L- is a biradical selected from the following ones —(CH$_2$)$_r$NR‴(CH$_2$)$_s$—

—(CH$_2$)$_r$NR‴(CH$_2$)$_s$NR″″(CH$_2$)$_t$—.

11. The compound according to claim 10, wherein -L- is the biradical —(CH$_2$)$_r$NR‴(CH$_2$)$_s$—, R‴ is methyl, and both r and s are 3.

12. The compound according to claim 10, wherein -L- is the biradical —(CH$_2$)$_r$NR‴(CH$_2$)$_s$NR″″(CH$_2$)$_t$—, both —R‴ and —R″″ are methyl; both r and t are 2, and s is an integer from 2 to 3.

13. The compound according to claim 1, which is selected from the group consisting of:

N-[3-[[3-[(9-acridinecarbonyl)amino]propyl]methylamino]propyl]-10H-indolo[3,2-b]quinoline-11-carboxamide (Ia);

N,N'-(4-methyl-4-azaheptamethylene)-di-(10H-indolo[3,2-b]quinoline-11,11'-carboxamide) (Ib);

N-[3-[3-[[2-(1,3-dioxo-(2,3-dihydro)-1H-benzo[de]isoquinolinyl]propyl]methylamino]propyl]-10H-indolo[3,2-b]quinoline-11-carboxamide (Ic);

N-[3-[[3-[(2-phenyl-4-quinolinecarbonyl)amino]propyl] methylamino]propyl]-10H-indolo[3,2-b]quinoline-11-carboxamide (Id);

N,N'-(3,7-dimethyl-3,7-diazanonamethylene)-di-(10H-indolo[3,2-b]quinoline-11,11'-carboxamide) (Ie);

N-[(9-acridinecarbonyl)-3,7,10-triaza-3,7-dimethyldecyl]-10H-indolo[3,2-b]quinoline-11-carboxamide (If);

N,N'-(3,6-dimethyl-3,6-diazaoctamethylene)-di-(10H-indolo [3,2-b]quinoline-11-11'-carboxamide (Ig);

N-[(9-acridinecarbonyl)-3,6-dimethyl-3,6-diazaoctamethylene]-10H-indolo[3,2-b]quinoline-11-carboxamide (Ih);

N-[[1,3-dioxo-(2,3-dihydro)-1H-benzo[de]isoquinolyl]-3,6-dimethyl-3,6-diazaoctamethylene]-10H-indolo[3,2-b]quinoline-11-carboxamide (Ii);

N-[[1,3-dioxo-(2,3-dihydro)-1H-benzo[de]isoquinolyl]-3,7,10-triaza-3,7-dimethyldecyl]-10H-indolo[3,2-b]quinoline-11-carboxamide (Ij);

N,N'-(4-methyl-4-azaheptamethylene)-di-(5-methyl-5H-indolo[3,2-b]quinoline-11,11'-carboxamide) (Im);

N,N'-(4-methyl-4-azaheptamethylen)-di-(5-methyl-5H-indolo[3,2-b]quinoline-11,11'-amine (Iq);

N,N'-(3,7-dimethyl-3,7-diazanonamethylene)-di-(5-methyl-5H-indolo[3,2-b]quinoline-11,11'-carboxamide) (Iy);

N,N'-(3,6-dimethyl-3,6-diazaoctamethylene)-di-(5-methyl-5H-indolo[3,2-b]quinoline-11,11'-carboxamide) (Iz);

(3,7-diazanonamethylene)-di-(10H-indolo [3,2-b]quinoline-11,11'-carboxamide (Iaa);

N,N'-(3,7-dimethyl-3,7-diazanonamethylene)-di-(5-methyl-5H-indolo[3,2-b]quinoline-11,11'-amine (Iab); and N,N'-(3,6-dimethyl-3,6-diazaoctamethylene)-di-(5-methyl-5H-indolo[3,2-b]quinoline-11,11'-amine (Iac).

14. A method for the treatment of cancer selected from the group consisting of lung cancer and leukemia which comprises administering to a subject a therapeutically effective amount of a compound of formula (I)

$$G_1\text{-}L\text{-}G_2 \quad (I)$$

or a pharmaceutically acceptable salt thereof, wherein:

-$G_1$ is a radical (II)

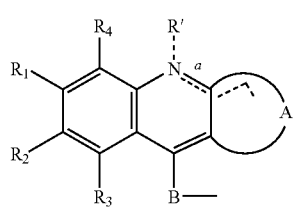
(II)

wherein —R' is an electron pair or a ($C_1$-$C_3$)-alkyl radical; with the condition that (i) when —R' is an electron pair, a is a N=C double bond and the fused ring

is the biradical

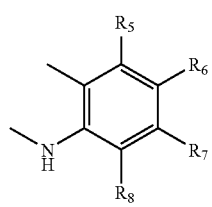

thus radical (II) is (IIa'), and

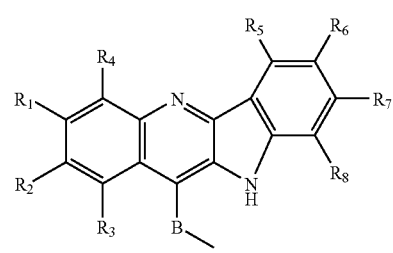
(IIa')

(ii) when —R' is a ($C_1$-$C_3$)-alkyl radical, a is a N—C single bond and the fused ring is the triradical

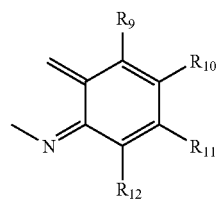

thus radical (II) is (IIa");

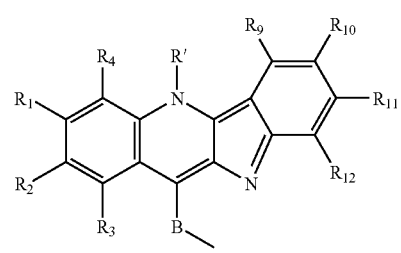
(IIa")

wherein —$R_1$ to —$R_{12}$ represent radicals, same or different, selected from the group consisting of H, ($C_1$-$C_4$)-alkyl, ($C_1$-$C_4$)-alkoxy, ($C_1$-$C_4$)-alkylamino, phenyl, F, Cl, Br, amino, hydroxy, and nitro;

and wherein —B— is a biradical selected from the group consisting of —CONH—, —$NR_{13}$—, —O—, —$(CH_2)_n$NH—, and —$(CH_2)_n$O—; wherein —$R_{13}$ is selected from the group consisting of H, ($C_1$-$C_4$)-alkyl, ($C_1$-$C_4$)-alkoxy and ($C_1$-$C_4$)-alkylamino; and n is an integer from 1 to 3;

-L- is a covalent linking biradical selected from the following ones;

—$(CH_2)_r$NR'''$(CH_2)_s$—

—$(CH_2)_r$NR'''$(CH_2)_s$NR''''$(CH_2)_t$— wherein —R''' and —R'''' are radicals, same or different, selected from the group consisting of H and ($C_1$-$C_3$)-alkyl; r is an integer from 1 to 3; s is an integer from 1 to 3; t is an integer from 1 to 3; and -$G_2$ is a radical selected from a radical of formula (II), the N-radical of 1,8-naphthalimide, the C4-radical of 2-phenylquinoline, and the C9-radical of acridine.

15. A pharmaceutical composition comprising a therapeutically effective amount of the compound as defined claim 1, together with appropriate amounts of pharmaceutical excipients or carriers.

16. A method of manufacturing a composition of matter comprising formula (I) and one of the following processes:

Process I:

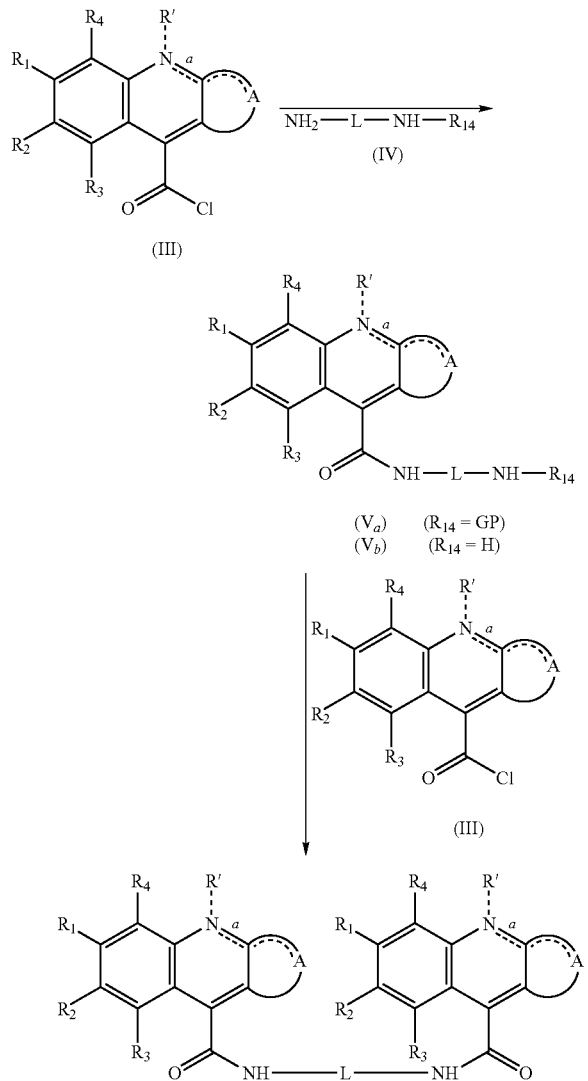

when biradical —B— in -G$_1$ is —CONH— and -G$_2$ is not an N-radical of 1,8-naphtalimide; and
wherein GP represents an amino protective group and wherein formula (IV) is a monoprotected bis-amine; or Process II:

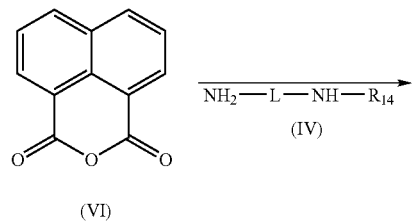

-continued

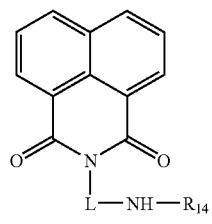

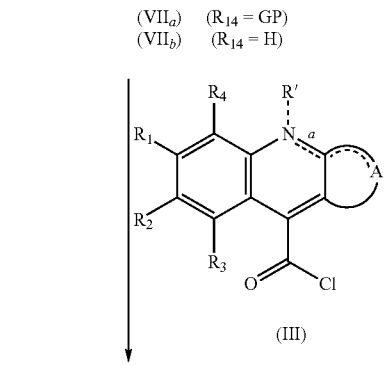

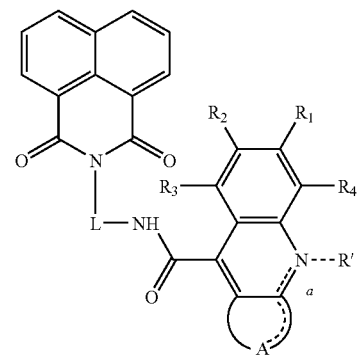

when biradical —B— in -G$_1$ is —CONH— and -G$_2$ is 1,8-naphtalimide; and
wherein GP represents an amino protective group and wherein formula (IV) is a monoprotected bis-amine; or Scheme III:

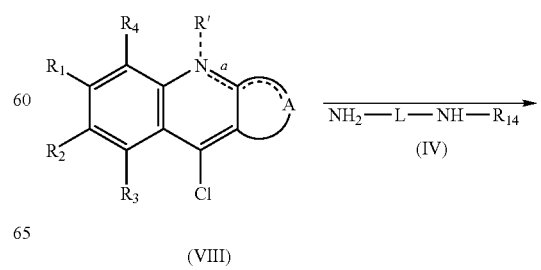

-continued
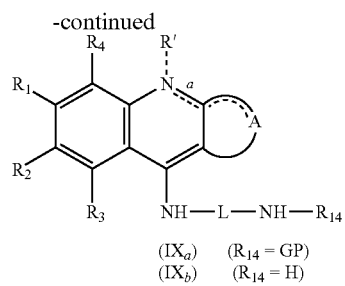
(IX$_a$) (R$_{14}$ = GP)
(IX$_b$) (R$_{14}$ = H)
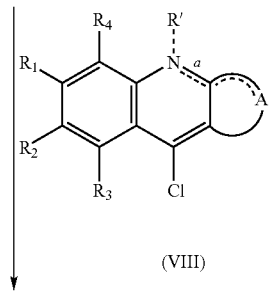
(VIII)
-continued
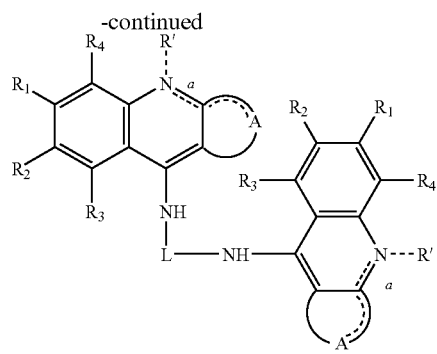
when biradical —B— is a biradical selected from a group of: —NR$_{13}$—, —O—, —(CH$_2$)$_n$NH, and —(CH$_2$)$_n$O—; and
wherein GP represents an amino protective group.
* * * * *